(12) United States Patent
Strickler et al.

(10) Patent No.: US 10,690,594 B2
(45) Date of Patent: Jun. 23, 2020

(54) OPTICAL SENSING DEVICE AND METHOD IN A LIQUID TREATMENT SYSTEM

(71) Applicant: OptikTechnik LLC, Milwaukee, WI (US)

(72) Inventors: Johann Rudi Strickler, Milwaukee, WI (US); Jose Antonio Ramirez, Vernon Hills, IL (US)

(73) Assignee: OptikTechnik LLC, Milwaukee, WI (US)

( * ) Notice: Subject to any disclaimer, the term of this patent is extended or adjusted under 35 U.S.C. 154(b) by 125 days.

(21) Appl. No.: 15/265,504

(22) Filed: Sep. 14, 2016

(65) Prior Publication Data
US 2017/0074793 A1     Mar. 16, 2017

Related U.S. Application Data

(60) Provisional application No. 62/218,238, filed on Sep. 14, 2015.

(51) Int. Cl.
*G01N 21/49* (2006.01)
*G01N 15/14* (2006.01)
(Continued)

(52) U.S. Cl.
CPC ......... *G01N 21/49* (2013.01); *G01N 15/0227* (2013.01); *G01N 15/1434* (2013.01);
(Continued)

(58) Field of Classification Search
CPC .... G01N 21/49; G01N 15/0227; G01N 21/51; G01N 21/52; G01N 15/1431; G01N 2015/1447; G01N 2015/1493; G01N 2021/8416; G01N 21/6456; G01N 33/18; G01N 21/53; G01N 21/82; G01N 15/1434; G01N 15/136; G01N 2015/144; G01N 2015/145; G01N 2015/1454; G01N 221/8416; G01N 15/00; G01N 15/0205;
(Continued)

(56) References Cited

U.S. PATENT DOCUMENTS 3,328,587 A * 6/1967 Brown ................. B07C 5/3425
                                              250/204
3,879,615 A    4/1975 Moser
(Continued)

OTHER PUBLICATIONS

Search Report of the International Searching Authority for Application No. PCT/US2016/051741 dated Nov. 29, 2016 (2 pages).
(Continued)

*Primary Examiner* — Joseph W Drodge
(74) *Attorney, Agent, or Firm* — Michael Best & Friedrich LLP

(57) ABSTRACT

An optical sensing and control device includes a light source emitting a light beam and an optical component in communication with the light beam. The optical component is configured to move the light beam in a plane. The plane extends into an area such that the light beam interacts with particles in the area producing a scattering of the light beam. The optical sensing and control device also includes a photodetector in communication with the particles within the plane. The photodetector configured to generate image data in response to the scattering of the light beam.

20 Claims, 16 Drawing Sheets

(51) Int. Cl.
*G01N 21/82* (2006.01)
*G01N 21/51* (2006.01)
*G02B 26/12* (2006.01)
*G01N 33/18* (2006.01)
*G01N 15/02* (2006.01)
*G02B 26/10* (2006.01)
*H04N 7/18* (2006.01)
*G01N 21/84* (2006.01)
*G01N 21/64* (2006.01)

(52) U.S. Cl.
CPC ............. *G01N 21/51* (2013.01); *G01N 21/82* (2013.01); *G02B 26/105* (2013.01); *G02B 26/12* (2013.01); *C02F 2201/005* (2013.01); *G01N 21/6456* (2013.01); *G01N 33/18* (2013.01); *G01N 2015/1447* (2013.01); *G01N 2015/1493* (2013.01); *G01N 2021/8416* (2013.01); *H04N 7/183* (2013.01)

(58) Field of Classification Search
CPC ....... G01N 15/0211; G01N 2015/0092; G01N 2015/0216; G01N 2015/0222; G01N 2015/0238; G01N 2015/03; G01N 2015/035; G02B 26/08; C02F 2201/005; C02F 1/008; C02F 1/685; C02F 1/686; C02F 1/687; C02F 2209/105; C02F 2209/11; H04N 7/183
USPC .................. 210/94, 96.1, 614, 709, 745; 356/335–338, 341, 437, 441, 442; 359/196.1, 210.1, 223, 1, 225.1, 226.1, 359/226.2
See application file for complete search history.

(56) References Cited

U.S. PATENT DOCUMENTS

| | | | | |
|---|---|---|---|---|
| 4,249,244 A * | 2/1981 | Shofner | ............... | G01N 21/274 250/573 |
| 4,396,286 A * | 8/1983 | Shofner | ............... | G01N 21/53 356/243.1 |
| 4,665,592 A * | 5/1987 | Kasai | ............... | B29C 45/26 24/600.9 |
| 4,885,473 A * | 12/1989 | Shofner | ............. | G01N 15/0205 250/574 |
| 4,900,435 A * | 2/1990 | Anderson | .......... | B01D 15/1892 210/198.2 |
| 5,255,089 A | 10/1993 | Dybas et al. | | |
| 5,256,866 A * | 10/1993 | Conversano | ....... | G06K 7/10881 235/462.49 |
| 5,363,190 A * | 11/1994 | Inaba | ..................... | G02B 21/32 250/251 |
| 5,456,102 A * | 10/1995 | Moorehead | ........ | G01N 15/0205 356/335 |
| 5,570,183 A | 10/1996 | Wiles | | |
| 5,576,827 A * | 11/1996 | Strickland | .......... | G01N 15/0211 356/336 |
| 5,906,732 A * | 5/1999 | Kohno | .................... | B07C 5/361 137/883 |
| 6,091,492 A | 7/2000 | Strickland et al. | | |
| 6,429,423 B1 | 8/2002 | Friedland et al. | | |
| 7,298,534 B2 * | 11/2007 | Islam | ...................... | G02B 5/32 359/1 |
| 8,753,891 B2 * | 6/2014 | Hart | ....................... | B01J 19/121 209/1 |
| 10,006,857 B2 * | 6/2018 | Marshall | ................ | G01N 21/51 |
| 2001/0014436 A1 | 8/2001 | Lemelson et al. | | |
| 2004/0021100 A1 | 2/2004 | Gouzman et al. | | |
| 2006/0208883 A1 | 9/2006 | Kong et al. | | |
| 2007/0155017 A1 * | 7/2007 | Wyatt | ................ | G01N 15/0255 436/45 |
| 2008/0043314 A1 * | 2/2008 | Hagler | ...................... | G01J 3/02 359/237 |
| 2009/0032449 A1 * | 2/2009 | Mueth | .................... | G02B 21/32 210/94 |
| 2012/0127456 A1 * | 5/2012 | Frojdh | .................. | G01N 21/05 356/51 |
| 2016/0160260 A1 * | 6/2016 | Marshall | .................. | C12Q 1/06 435/39 |
| 2016/0216204 A1 * | 7/2016 | Marshall | ................ | G01N 21/51 |

OTHER PUBLICATIONS

Written Opinion of the International Searching Authority for Application No. PCT/US2016/051741 dated Nov. 29, 2016 (10 pages).
Extended European Search Report from the European Patent Office for Application No. 16847233.0 dated Mar. 8, 2019 (15 pages).

* cited by examiner

OPTICAL SENSING DEVICE AND METHOD IN A LIQUID TREATMENT SYSTEM

CROSS-REFERENCE TO RELATED APPLICATIONS

This application claims priority to U.S. Provisional Patent Application No. 62/218,238 filed Sep. 14, 2015, the entire content of which is incorporated herein by reference.

FIELD OF THE INVENTION

The present invention relates to optical sensing devices, and, in some instances, to optical sensing devices in a liquid treatment system.

SUMMARY

In one embodiment, an optical sensing and control device includes a light source emitting a light beam and an optical component in communication with the light beam. The optical component is configured to move the light beam in a plane. The plane extends into an area such that the light beam interacts with particles in the area producing a scattering of the light beam. The optical sensing and control device also includes a photodetector in communication with the particles within the plane. The photodetector configured to generate image data in response to the scattering of the light beam.

In another embodiment, a method of determining a process variable of a compound contained within a control volume includes emitting a light beam from a light source toward an optical component, moving the light beam in a plane that extends into the compound such that the light beam interacts with the compound producing a scattering of the light beam, generating image data from the scattering of the light beam with a photodetector, and analyzing the image data to determine the process variable.

In yet another embodiment, a liquid treatment system includes a control volume containing a compound and an output device in communication with the control volume. The output device is configured to control a process variable of the compound. The liquid treatment system also includes an optical sensing and control device in communication with the compound. The optical sensing and control device includes a light source emitting a light beam and an optical component in communication with the light beam. The optical component is configured to move the light beam in a plane. The plane extends into the compound such that the light beam interacts with the compound producing a scattering of the light beam. The optical sensing and control device also includes a photodetector in communication with the compound within the plane. The photodetector is configured to detect the scattering of the light beam. The output device is configured to control the process variable based on the scattering of the light selected from the group consisting of changing a temperature of the compound, introducing a chemical into the control volume, changing a mixing rate of the compound, controlling an inlet valve of the control volume, and controlling an outlet valve of the control volume.

Other features and aspects of the invention will become apparent by consideration of the following detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

Figure 1:
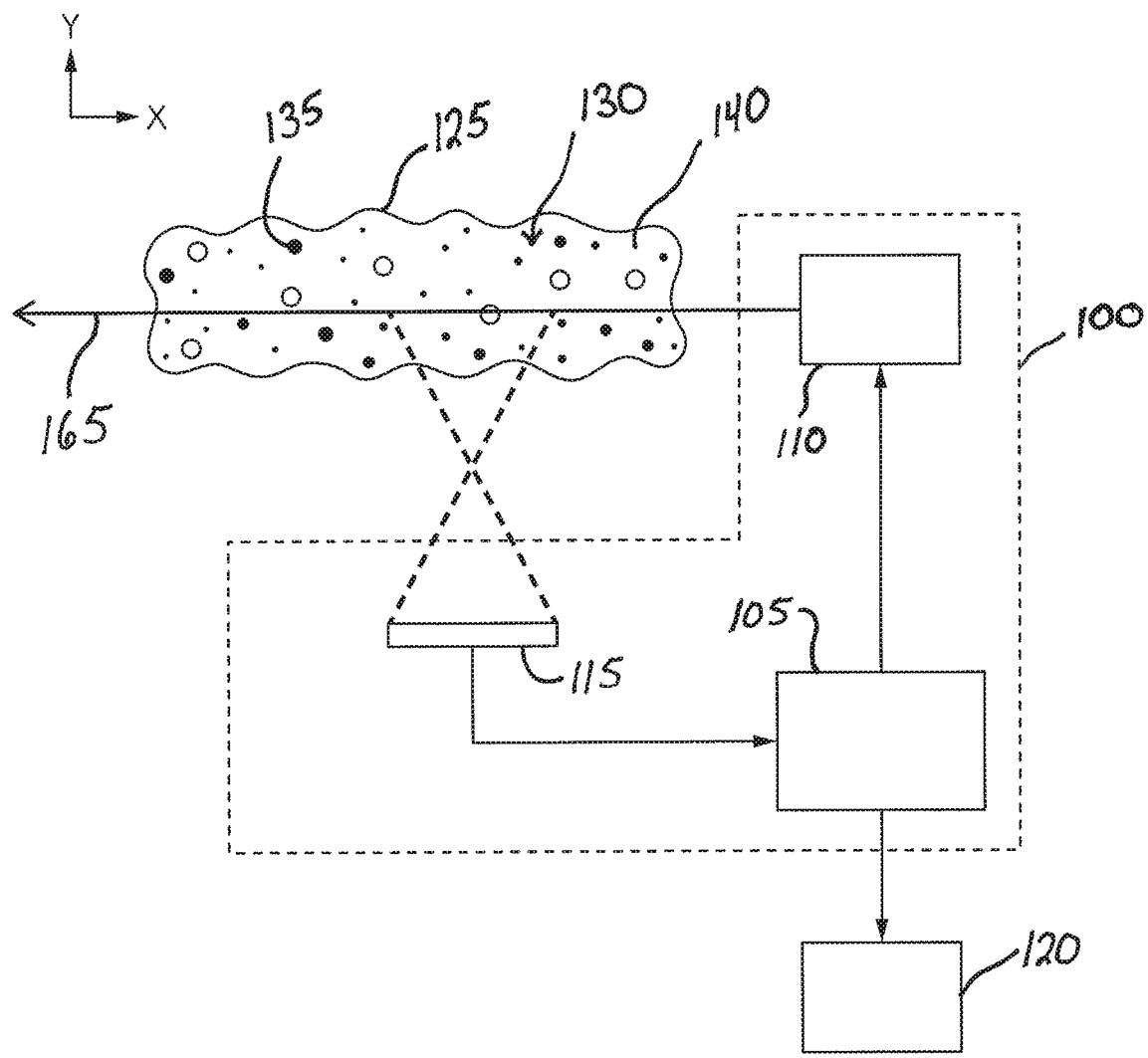
FIG. 1 illustrates an optical sensing and control device according to an embodiment of the invention in communication with a control volume and an output device.

FIG. 1 illustrates an optical sensing and control device 100 (referred as the optical device 100 herein) including a control assembly 105, a light plane generator 110, and a photodetector 115. The illustrated control assembly 105 is in communication with the light plane generator 110, the photodetector 115, and an output device 120. The photodetector 115 is in communication with a control volume or area 125 containing a compound 130. In the illustrated embodiment, the compound 130 includes particles 135 (e.g., solid particles) suspended within a liquid 140. In some embodiments, the compound 130 is a gas and liquid compound or a gas and solid compound. In some embodiments, a more than two-component compound may be contained within the control volume 125, such as a solid, liquid, and gas compound. In further embodiments, the compound 130 may include a same phase compound, e.g., two different types of gases, two different types of liquids, two different types of solids, etc. In other words, the compound 130 may include various combinations of components of various types.

Figure 2:
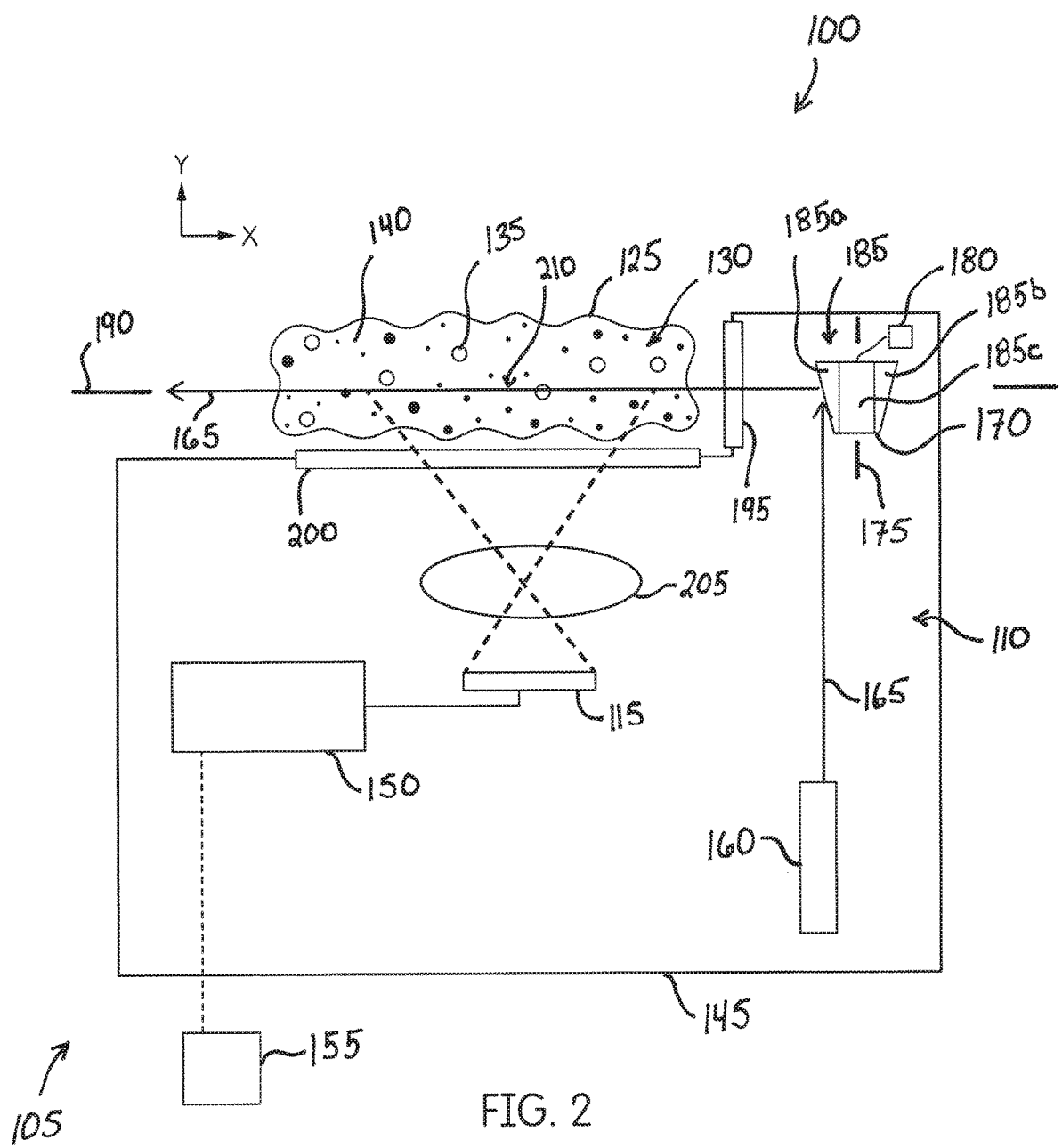
FIG. 2 illustrates the optical sensing and control device of FIG. 1 including a light plane generator that produces a light beam and directs the light beam within the control volume for the light beam to interact with a compound contained within the control volume.

With reference to FIG. 2, the optical device 100 includes a sealed housing 145 supporting the light plane generator 110, the photodetector 115, and an electronic processor 150 of the control assembly 105 that is in communication with the photodetector 115. In the illustrated embodiment, the housing 145 generally includes dimensions of 4 inches (in) by 3 in by 3 in (e.g., 36 cubic inches); however, in other embodiments, the housing 145 may be less than or greater than 36 cubic inches. The illustrated control assembly 105 includes the electronic processor 150 and a controller 155 located externally from the housing 145. The illustrated controller 155 can be a programmable controller or a personal computer (e.g., a laptop, smartphone, etc.) that is in communication with the electronic processor 150 and the output device 120. In another embodiment, the controller 155 and the electronic processor 150 may be combined into one controller supported within the housing 145. In another embodiment, a first housing may support the light plane generator 110 and a second housing 145, which is separate from the first housing, may support the photodetector 115 and at least a portion of the control assembly 105. The illustrated light plane generator 110 includes a light source 160, e.g., a diode, a laser diode, etc., emitting a light beam 165 toward and into contact with an optical component 170 in the XY plane, as shown in FIG. 2. In some embodiments, an optical lens is positioned between the light source 160 and the optical component 170 to focus and/or increase an intensity of the light beam 165 toward the optical component 170. The illustrated optical component 170 is a polygonal-shaped (e.g., hexagonal, octagonal, triangular, etc.) mirror rotatable about an axis 175 by a motor 180 at an angular velocity of about 25,000 revolutions per minute (RPM). In another embodiment, the optical component 170 may rotate at an angular velocity selected from a range of about 1 RPM and about 60,000 RPM, or selected from any other range therebetween. The selected angular velocity may be selected based on the compound being scanned. For example, a relatively static compound (e.g., rock formation) may be scanned at an angular velocity of 1 RPM, while a compound that is dynamically changing may be scanned at a higher angular velocity. In another embodiment, the optical component 170 may be driven about the axis 175 by pneumatic power, e.g., by a pressurized air jet.

Figure 3:
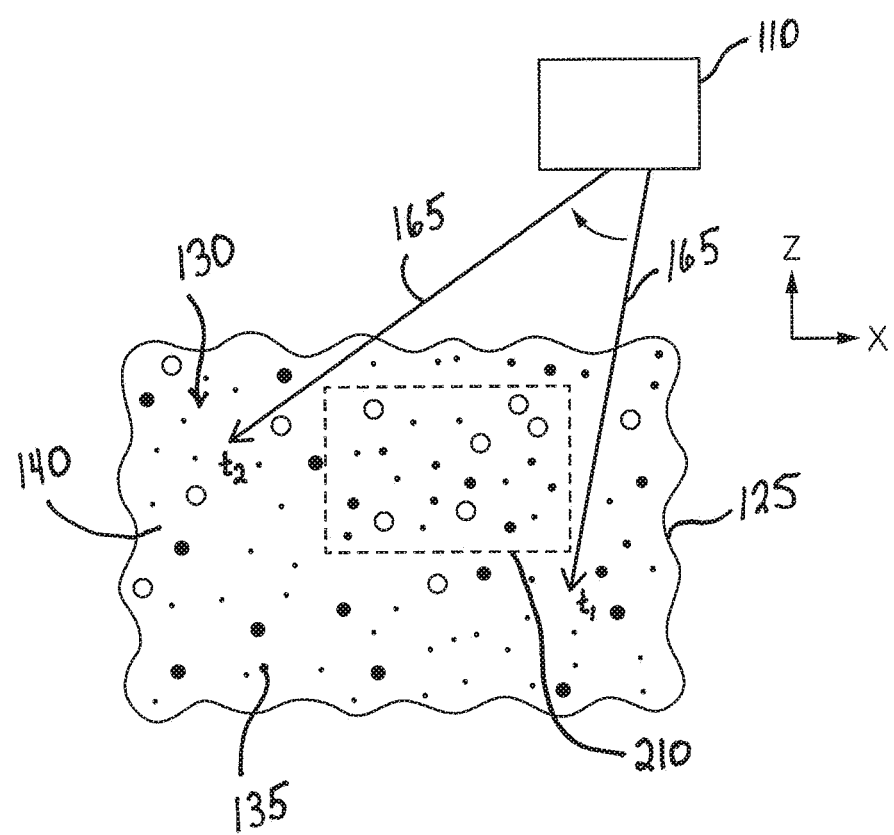
FIG. 3 illustrates the light plane generator of FIG. 2 operable to move the light beam within the control volume in an optical plane from a first position to a second position.

In the illustrated embodiment, the optical component 170 includes a plurality of planar surfaces 185 that are angled relative to each other and each planar surface 185 is configured to reflect the light beam 165 in a desired direction as the light beam 165 contacts the optical component 170. An example of such an optical component may be found in existing laser copy/scan printers. In other embodiments, the optical component 170 may be a polygonal-shaped prism rotatable about the axis 175 and configured to refract the light beam 165 in a desired direction. In the illustrated embodiment, the axis 175 is parallel to the light beam 165 emitted from the light source 160 and in response to the light beam 165 contacting the optical component 170, the light beam 165 is directed into an optical plane 190 perpendicular to the axis 175. The optical plane 190 is within the XZ plane and extends into the control volume 125, as shown in FIG. 3 (e.g., the XY plane is perpendicular to the XZ or optical plane 190). In another embodiment, the light beam 165 and/or the optical plane 190 may be obliquely angled relative to the axis 175. The optical component 170 is configured to redirect the light beam 165 within the optical plane 190 and is also configured to move the light beam 165 within the optical plane 190. Specifically, after the light beam 165 contacts the optical component 170, the light beam 165 is redirected to travel through a first window 195 of the housing 145 to extend into the control volume 125. Moreover, because the optical component 170 rotates as the light beam 165 contacts the optical component 170, the optical component 170 also moves the light beam 165 within the optical plane 190 at a linear velocity proportional to the angular velocity of the optical component 170. With reference to FIG. 3, the light beam 165 moves within the optical plane 190 from a first position $t_1$ toward a second position $t_2$. In particular, as the light beam 165 initially contacts a first planar surface 185a (FIG. 2) of the optical component 170, the light beam 165 is directed to the first position $t_1$. As the optical component 170 rotates, the first planar surface 185a moves relative to the light beam 165 to change the angle at which the light beam 165 reflects off of the optical component 170 so that the light beam 165 moves toward the second position $t_2$. The light beam 165 reaches the second position $t_2$ at a moment before the light beam 165 ceases contact with the first planar surface 185a to contact an adjacent second planar surface 185b (FIG. 2). Once the light beam 165 initially contacts the second planar surface 185b, the light beam 165 again starts at the first position $t_1$ to move towards the second position $t_2$. The movement of the light beam 165 from the first position $t_1$ to the second position $t_2$ repeats with the light beam 165 contacting each planar surface 185 to provide a scanning motion effect of the light beam 165 within the optical plane 190. Stated another away, the frequency at which the light beam 165 illuminates the optical plane 190 is dependent upon the angular velocity of the optical component 170.

With continued reference to FIGS. 2 and 3, the photodetector 115 is in visual communication with the optical plane 190 through a second window 200 of the housing 145. In the illustrated embodiment, the first and second windows 195, 200 are oriented perpendicular to each other. In another embodiment, the first and second windows 195, 200 may be formed as a single window (e.g., an L-shaped window). An optical lens 205 is positioned between the second window 200 and the photodetector 115 to focus the photodetector 115 on a target area 210 of the optical plane 190. The target area 210 is a portion of the optical plane 190 between the first and second positions $t_1$, $t_2$ of the light beam 165 and can include dimensions of 10 centimeters (cm) by 10 cm (e.g., 100 squared centimeters). In other embodiments, the target area 210 may be greater or less than 100 squared centimeters. The illustrated photodetector 115 includes a 2 to 3 megapixel resolution; however, in other embodiments, the megapixel resolution of the photodetector 115 may be less than 2 or greater than 3. In addition, the photodetector 115 is operable with a relatively lower power requirement, e.g., 5 volts or less that is supplied by AA batteries, AAA batteries, or the like. In the illustrated embodiment, the photodetector 115 is focused on the target area 210 at a 90 degree angle relative to the optical plane 190. In another embodiment, the photodetector 115 may be focused on the target area 210 at an angle between 0 degrees and 180 degrees relative to the optical plane 190. In further embodiments, a plurality of photodetectors 115 may be positioned around the target area 210 at different angles.

Figure 4:
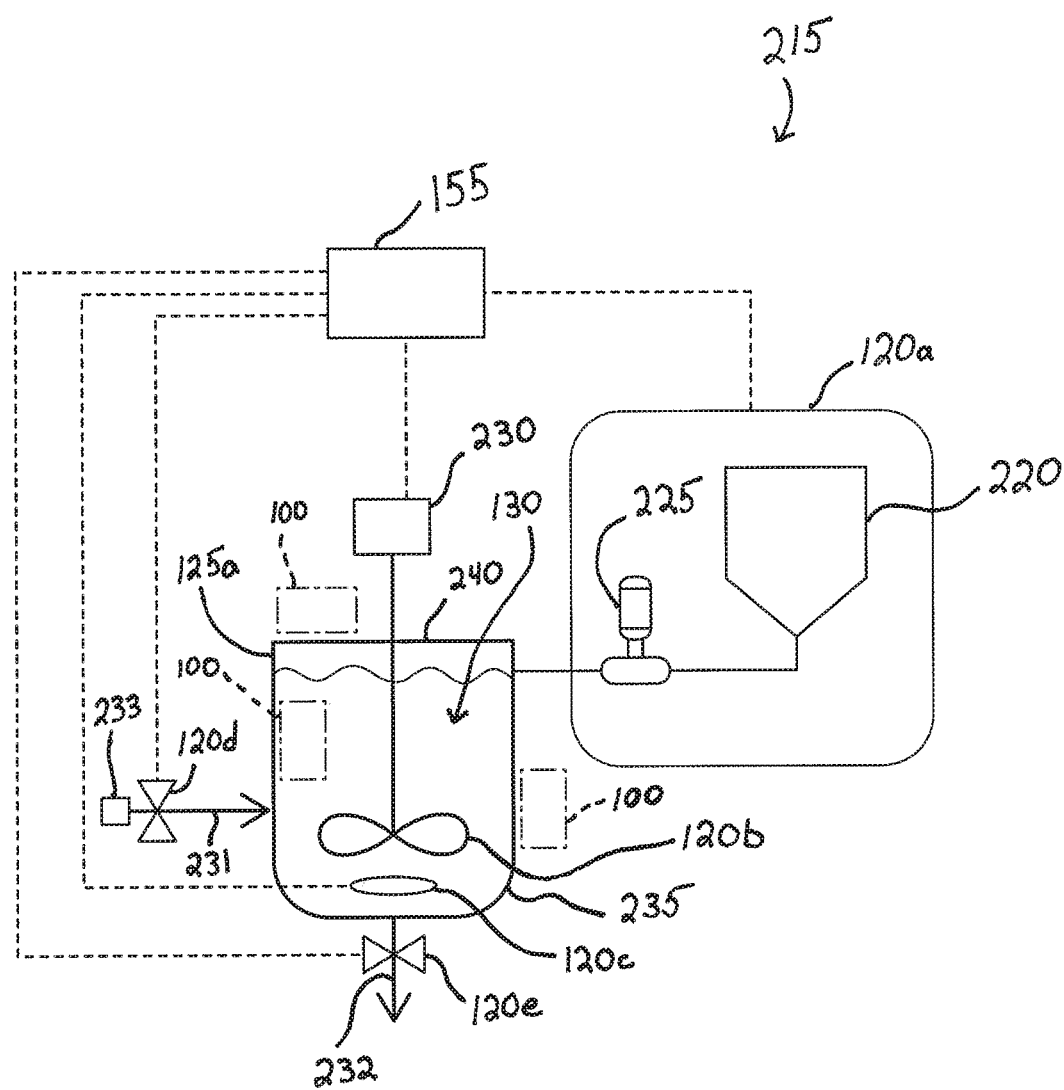
FIG. 4 illustrates the optical sensing and control device of FIG. 2 operable within a liquid treatment system.

With reference to FIG. 4, a liquid treatment system 215 includes the optical sensing and control device 100 operable to control coagulation for treatment of effluent water. In particular, the liquid treatment system 215 includes the control volume 125 (illustrated as a tank 125a) supporting the compound 130 (e.g., the effluent water). The liquid treatment system 215 also includes the controller 155 that is in communication with a first output device 120a (illustrated as a chemical dispenser 220 including an actuation valve 225 fluidly coupled to the tank 125a). The controller 155 is also in communication with other output devices, such as agitation blades 120b positioned within the tank 125a and coupled to a motor 230, a heater 120c positioned within or adjacent the tank 125a, an inlet valve 120d operable to introduce the compound 130 into the tank 125a through an inlet passageway 231, and an outlet valve 120e operable to discharge at least a portion of the compound 130 from the tank 125a through an outlet passageway 232. For example, in one embodiment, the liquid 140 of the compound 130 may be discharged from the tank 125a through the outlet valve 120e, and in another embodiment, the particles 135 may be discharged from the tank 125a through the outlet valve 120e. The optical sensing and control device 100 can be selectively located in a plurality of positions relative to the tank 125a, can be portable relative to the tank 125a, or can be coupled to the tank 125a. For example, the optical sensing and control device 100 may be submerged within the compound 130 (e.g., the housing 145 is waterproof), coupled to an outer surface 235 of the tank 125a (e.g., if the tank 125a is transparent or includes a window), located adjacent an opening 240 of the tank 125a, externally or internally coupled to the inlet passageway 231, and/or externally or internally coupled to the outlet passageway 232. FIG. 4 illustrates the optical device 100 in a few illustrative locations. In the embodiment with the optical sensing device 100 coupled to the inlet passageway 231, the optical sensing device 100 may also be in communication with a sampling region 233 of the inlet passageway 231, which may be located upstream or downstream of the inlet valve 120d. In some embodiments, the portability of the optical device 100 allows for monitoring of multiple tanks 125a, and/or multiple areas within a single tank 125a. In some embodiments, the tank 125a may be a closed volume (i.e., the opening 240 is omitted).

Figure 5:
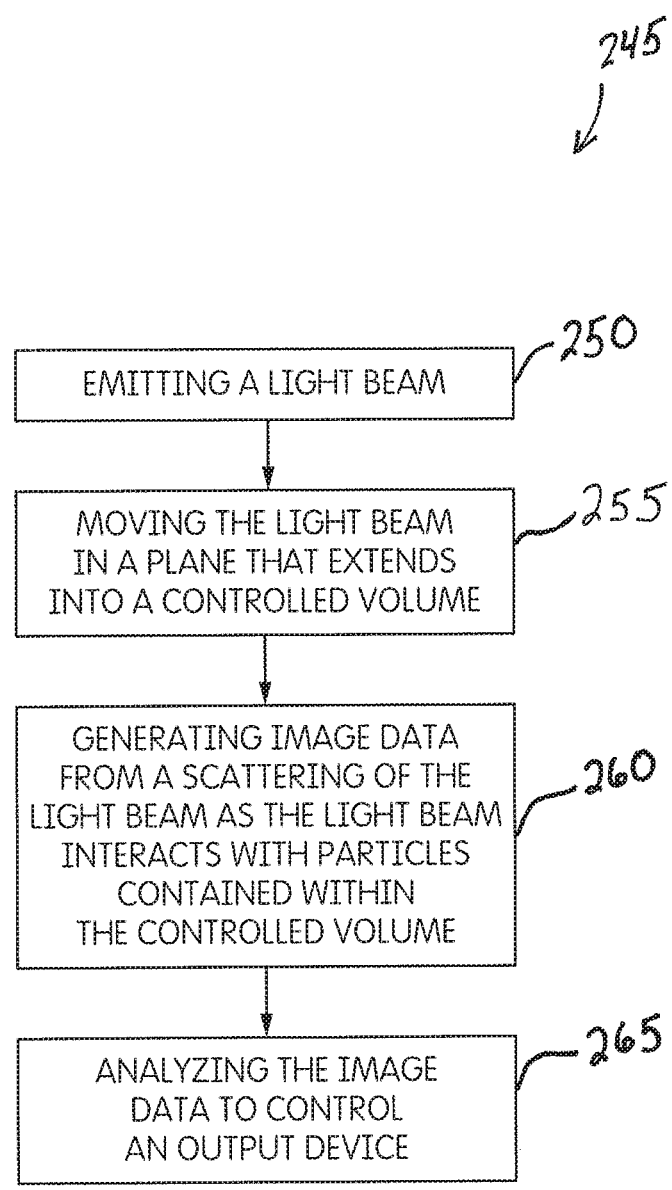
FIG. 5 illustrates a method of determining a process variable of the compound contained within the control volume of the liquid treatment system of FIG. 4.

FIG. 5 illustrates a feedback method 245 of operating the liquid treatment system 215. The controller 155 is configured to operate the light source 160 to emit the light beam 165 toward the optical component 170 (step 250). As the optical component 170 rotates, the light beam 165 is directed into and moves in the optical plane 190 to interact with the compound 130 (step 255). As the light beam 165 continuously moves from the first position $t_1$ to the second position $t_2$, the light beam 165 interacts (e.g., collides) with the particles 135 (comprising of micro and macro particulates and aggregates) that are at least partially within the optical plane 190 resulting in a scatter of the light beam 165 in a plurality of directions (e.g., scatter of the light beam 360 degrees relative to the optical plane 190). Because the photodetector 115 is perpendicular to the optical plane 190 and is focused on the target area 210, the photodetector 115 detects scatter of the light beam 165 within the target area 210 that is generally perpendicular to the optical plane 190. In the embodiments that include the photodetector 115 oriented at an oblique angle relative to the optical plane 190, the photodetector 115 will detect scatter of the light beam 165 within the target area 210 at the oblique angle.

In the illustrated embodiment, photodetector 115 includes an exposure time that is greater than or equal to the time the light beam 165 moves from the first position $t_1$ to the second position $t_2$. For example, in one embodiment, the photodetector 115 begins to detect the scatter of the light beam 165 when the light beam 165 is in the first position $t_1$, and temporarily stops detecting the scatter of the light beam 165 when the light beam 165 is in the second position $t_2$. During one exposure sequence (e.g., when the photodetector 115 starts to detect scatter to when the photodetector 115 temporarily stops detecting scatter), the photodetector 115 generates image data from the scattering of the light beam 165 (step 260).

The image data is then received by the control assembly 105 (made up of the electronic processor 150 and controller 155), which analyzes the image data to control an output device 120 (step 260). For example, the image data from the photodetector may be received by the electronic processor 150, and the electronic processor 150 generates an image including the image data (e.g., by grouping or compiling the image data into an image file). In the illustrated embodiment, the electronic processor 150 captures the image data of the photodetector 115 on a gray scale ranging from 0 (e.g., black) to 256 (e.g., white) to generate the image, which is similar to the image of the target area 210 as shown in FIG. 3. The gray scale can then be translated into absolute or relative states of aggregation of the compound 130. In other embodiments, the image data is captured in different gray scales (e.g., ranges different than 0-256) or in color.

As such, the image generated by the electronic processor 150 of the target area 210 is configured to be a representation of a process variable of the compound 130 contained within the tank 125a. The process variable of the compound 130 can be the size of the particles 135 suspended in the liquid 140, the amount of particles 135 within the target area 210, the transparency of the particles 135 within the target area 210, or other characteristics that define the compound 130. The controller 155 then receives the image from the electronic processor 150 and analyzes the image using image processing software (e.g., stored and executed on the controller 155).

Based on the analysis, the controller 155 controls at least one output device 120 (e.g., the actuation valve 225, the agitation blades 120b, the heater 120c, the inlet valve 120d, and/or the outlet valve 120e). For example, the controller 155 may manipulate the coagulation of the compound 130, thereby altering the process variable, by controlling an amount of chemical(s) introduced within the tank 125a that are contained within the chemical dispenser 220 by opening or closing the actuation valve 225. The controller 155 may alter the process variable of the compound 130 by controlling a mixing rate of the compound 130 by altering the velocity of the agitation blades 120b via the motor 230. The controller 155 may alter the process variable of the compound 130 by altering the temperature of the compound 130 by the heater 120c. The controller 155 may alter the process variable of the compound 130 by controlling how much compound 130 enters or exits the tank 125a via the inlet valve 120d or the outlet valve 120e, respectively.

Therefore, the optical sensing and control device 100 monitors the coagulation of the compound 130 within the tank 125a by detecting scattering of the light beam 165 interacting with the particles 135, analyzes the coagulation of the compound 130 by analyzing the image based on the image data, and controls the coagulation of the compound 130 by manipulating the process variable of the compound 130 by at least one output device 120 based on the image.

Furthermore, as a result of the optical component 170 rotating at such a fast angular velocity (e.g., 25,000 RPM), the light beam 165 moves from the first position $t_1$ to the second position $t_2$ at a high frequency. Accordingly, the photodetector 115 generates a large collection of image data in a certain time period allowing the controller 155 to generate images of the compound 130 made in-situ and in real-time. Also, the controller 155 generates the images without intrusively interacting with the compound 130. This large collection of images within a short period of time allows for narrow tolerances of the process variable of the compound 130, which improves efficiency of removing or separating the particles 135 suspended within the liquid 140 in the liquid treatment system 215.

In other embodiments, the method 245 may be a feed-forward method. In particular, the optical device 100 monitors the compound 130 upstream from the tank 125a (e.g., the compound 130 passing through the sample region 233 of the inlet passageway 231) to generate image data by the photodetector 115 (e.g., similar to step 260). The image data within the sample region 233 is configured to be a representation of a characteristic of the compound 130 entering the tank 125a through the inlet passageway 231. The electronic processor 150 then receives the image data and generates an image that is received by the controller 155. The controller 155 analyzes the image by utilizing a process model (e.g., mathematical, stochastic, empirical, etc. model) to predict how to control the process variable of the compound 130 contained within the tank 125a (e.g., similar to step 165). The controller 155 can then operate one or more of the output devices 120 based on information from the process model to control the process variable of the compound 130 contained within the tank 125a. Stated another way, the feed-forward method of the optical device 100 uses theoretical deduction to predict and control the process variable of the compound 130 contained within the tank 125a compared to the feedback method of the optical device 100 that uses empirical observations of the compound 130 contained within the tank 125a to control the process variable of the compound 130. In further embodiments, the liquid treatment system 215 may include at least one optical device 100 including a feedback method and at least one optical device 100 including a feed-forward method with both optical devices 100 in communication with each other to quickly and accurately control the process variable of the compound 130.

Embodiments of the optical device 100 and method 245 enables accurate control of the coagulation/flocculation process with minimal effort and cost, and without requiring an operator to have deep technical expertise. Given that coagulation and flocculation are employed in virtually all municipal and industrial wastewater treatment operations and in most drinking water systems drawing from surface waters, the optical device 100 could be used in a wide range of applications. The optical device 100 provides, in some embodiments, tighter, more effective control of chemical dosage, which may result in considerable cost savings and substantial reduction of the carbon footprint of these operations.

In addition, precipitation of phosphorous with chemicals is heavily reliant on a properly operating coagulation and flocculation process. More precise, on-line control of the coagulation and flocculation process enables operators across all industrial sectors, to consistently achieve lower phosphate levels in their effluent. The simplicity and cost-effectiveness of the optical device 100 and method 245 described herein renders chemical precipitation of phosphorous more easily accessible to small and medium operators that cannot afford expensive biological treatment. This will help federal and state regulatory agencies in establishing newer strict phosphorous discharge limit, or enforcing pending or existing ones.

Embodiments of the optical device 100 allow for monitoring the size distribution and number densities of a suspension undergoing aggregation with a simple, low cost instrument that can be interfaced with chemical dosing equipment, ensuring real-time control of the coagulation/flocculation process. The sensor may be non-invasive, meaning that it can be used to monitor flocculation in-situ, without having to draw/dilute samples or pass them to a side-sampling chamber.

Embodiments of the optical device 100 and the method 245 may also be used in water/wastewater treatment systems based on a variation of microflotation, such as those used in small/medium size industrial dischargers. The optical device 100 provides an accurate sensing and control system to monitor influent/effluent quality and control overall flotation process performance.

Embodiments of the optical device 100 and the method 245 can also be used in other installations where the efficient reuse of water or the disposal of wastewater is important. This includes federal research labs, military bases, and maritime equipment and installations.

Embodiments of the optical device 100 and the method 245 can significantly improve the efficiency of both recirculating aquaculture systems (RAS) and flow-through systems (FTS). Real-time, online control of the coagulation process allows its wide application in aquaculture in practice. Efficient chemical coagulation allows more efficient solids and phosphorous removal from reuse and effluent water. This results in higher water reuse rates for RAS, while allowing improved management of effluent discharges in both RAS and FTS. More efficient solids removal by pre-treatment with coagulation chemicals allows for smaller clarifiers/gravity settlers, longer filter/membrane run times and more efficient filter backwashing. It also allows more cost-effective control of key regulated pollutants such as biochemical oxygen demand (BOD), total suspended solids (TSS), and total phosphorous. Overall, it allows the operation to maintain lower carbon and water footprints.

Embodiments of the optical device 100 and method 245 have various other applications including particle-based measurements including the measuring of droplets in liquids, solids in liquids, liquid in liquids, solids in gas, and the like. Measurements may be of the state of aggregation of particles, dissolution of particles, degree of suspension of particles, size distribution of particles, and other particle characteristics.

Another application of the optical device 100 and the method 245 includes coagulation/flocculation processes providing accurate, rapid-response control of the coagulation/flocculation process where the raw water exhibit high variability in color, turbidity, or solids, pH and/or temperature or flow rates, particularly for installations that cannot afford expensive control systems based on the streaming current principle or that do not have access to knowledgeable operators with experience in jar testing or pilot filter analysis (e.g., small water treatment facilities drawing from surface waters, small/medium industrial wastewater treaters with highly variable processes).

Another application of the optical device 100 and the method 245 includes finished water quality monitor to enable monitoring of finished water quality, such as for small drinking water systems, as a monitor for suspended coliform, Giardia, or Cryptosporidium. The optical device 100 can be utilized as an on-line monitoring system that can trigger the appropriate alarms on detection of particles suspected to be pathogens that may have made it through the filtration units.

Another application of the optical device 100 and the method 245 includes ballast monitoring of water within or near a ballast of a ship or vessel and counting particle density for volume and particle identification.

Another application of the optical device 100 and the method 245 includes analysis of particles in emissions, such as smoke stacks or automotive exhaust emissions.

Another application of the optical device 100 and the method 245 includes analysis and detection of ice concentration in the air or near airplanes and other airborne vehicles, e.g., to detect ice build-up that can have the potential to harm instruments and components of the plane.

Another application of the optical device 100 and the method 245 includes measuring particle distribution in a body of water (e.g., lake, ocean, etc.) for various purposes, such as detecting pollution levels for determining a desired water intake location (e.g., for manufacturing processes or human consumption) or detecting animals and food sources based on trace particles.

Another application of the optical device 100 and the method 245 includes industrial processing to characterize, monitor, and control crystallization processes in pharmaceutical, specialty chemical, and food manufacturing.

Another application of the optical device 100 and the method 245 includes characterizing, monitoring, and controlling paper fiber flocculation.

Another application of the optical device 100 and the method 245 includes characterizing, monitoring, and controlling emulsification processes in food processes, specialty chemicals, oil and gas, petrochemicals, and pharmaceutical processes.

Another application of the optical device 100 and the method 245 includes characterizing, monitoring, and controlling dissolution processes typical of those in manufacturing in food, specialty chemical, pharmaceutical processes, agricultural chemicals, cement, etc.

Figure 6:
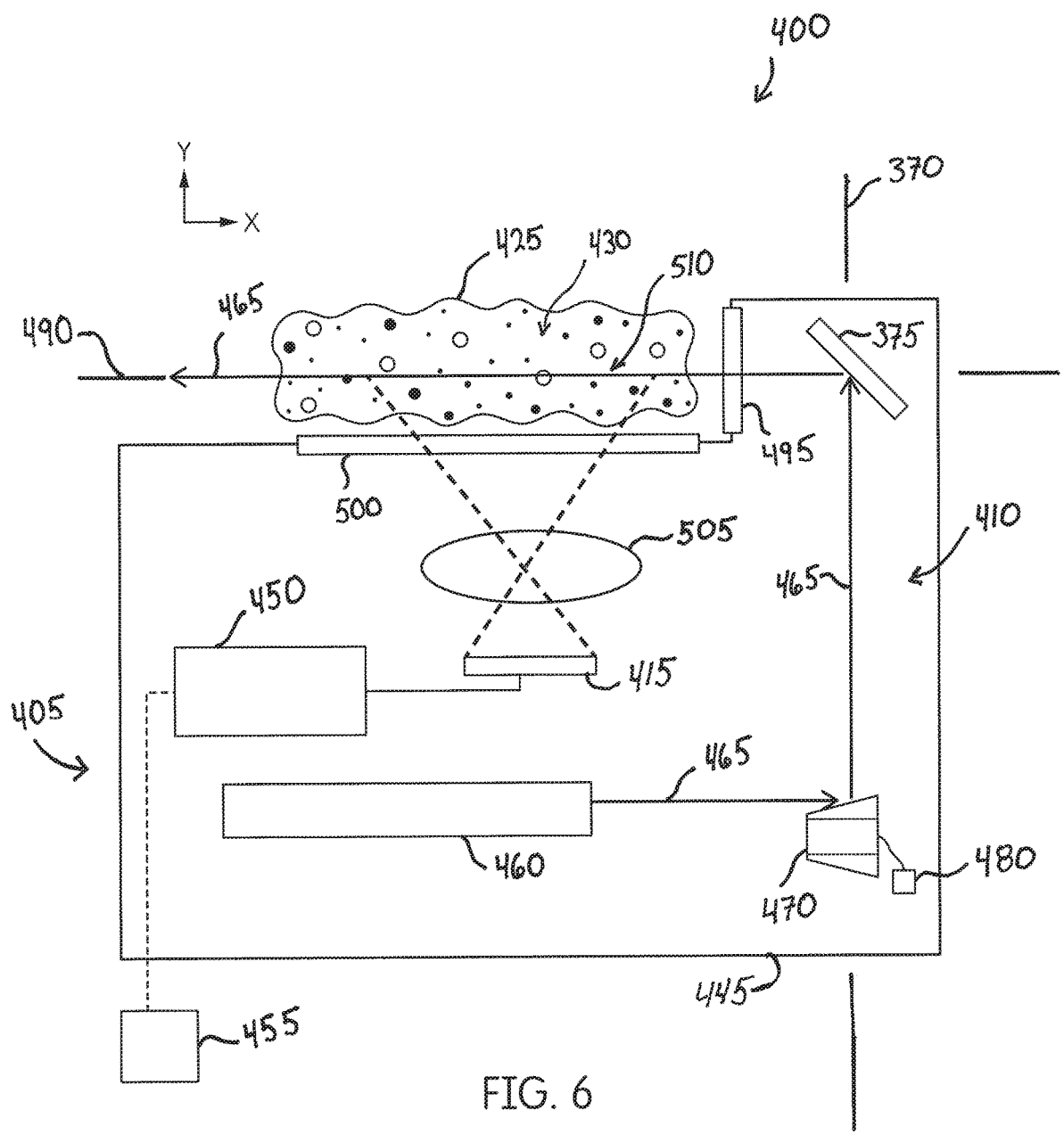
FIG. 6 illustrates an optical sensing and control device according to another embodiment of the invention.

FIG. 6 illustrates an optical device 400 according to another embodiment of the invention. The optical device 400 is similar to the optical device 100; therefore, like components have been given like reference numbers plus 300 and the description focuses on differences between the optical devices 100 and 400. In addition, components or features described with respect to only one or some of the embodiments of the optical device 400 are similarly applicable to other embodiments of the optical devices described herein, and vice versa.

The optical device 400 includes a housing 445 supporting a light plane generator 410 having a light source 460 and an optical component 470 driven by a motor 480, a photodetector 415, an optical lens 505, and a control assembly 405 having an electronic processor 450 and a controller 455. The light source 460 emits a light beam 465 toward the optical component 470 to direct and move the light beam 465 in an intermediate plane 370 extending between the optical component 470 and a reflector 375 (e.g., a planar mirror). Movement of the light beam 465 within the intermediate plane 370 is similar to the movement of the light beam 165 within the optical plane 190. Once the light beam 465 contacts the reflector 375, the reflector 375 directs the light beam 465 into an optical plane 490, which extends into a control volume 425 containing a compound 430, through a first window 495. As such, the light beam 465 travels through two planes before interacting with the compound 430. In the illustrated embodiment, the planes 370, 490 are perpendicular; however, in other embodiments, the planes 370, 490 may be obliquely angled. As the light beam 465 moves within the optical plane 490, the light beam 465 interacts with the compound 430 resulting in scatter of the light beam 465 that is detected by the photodetector 415 within a target area 510 through a second window 500. Accordingly, the photodetector 415 generates image data that is received by the electronic processor 450, and the electronic processor 450 generates an image that is received by the controller 455 for analysis and control based thereon.

Figure 7:
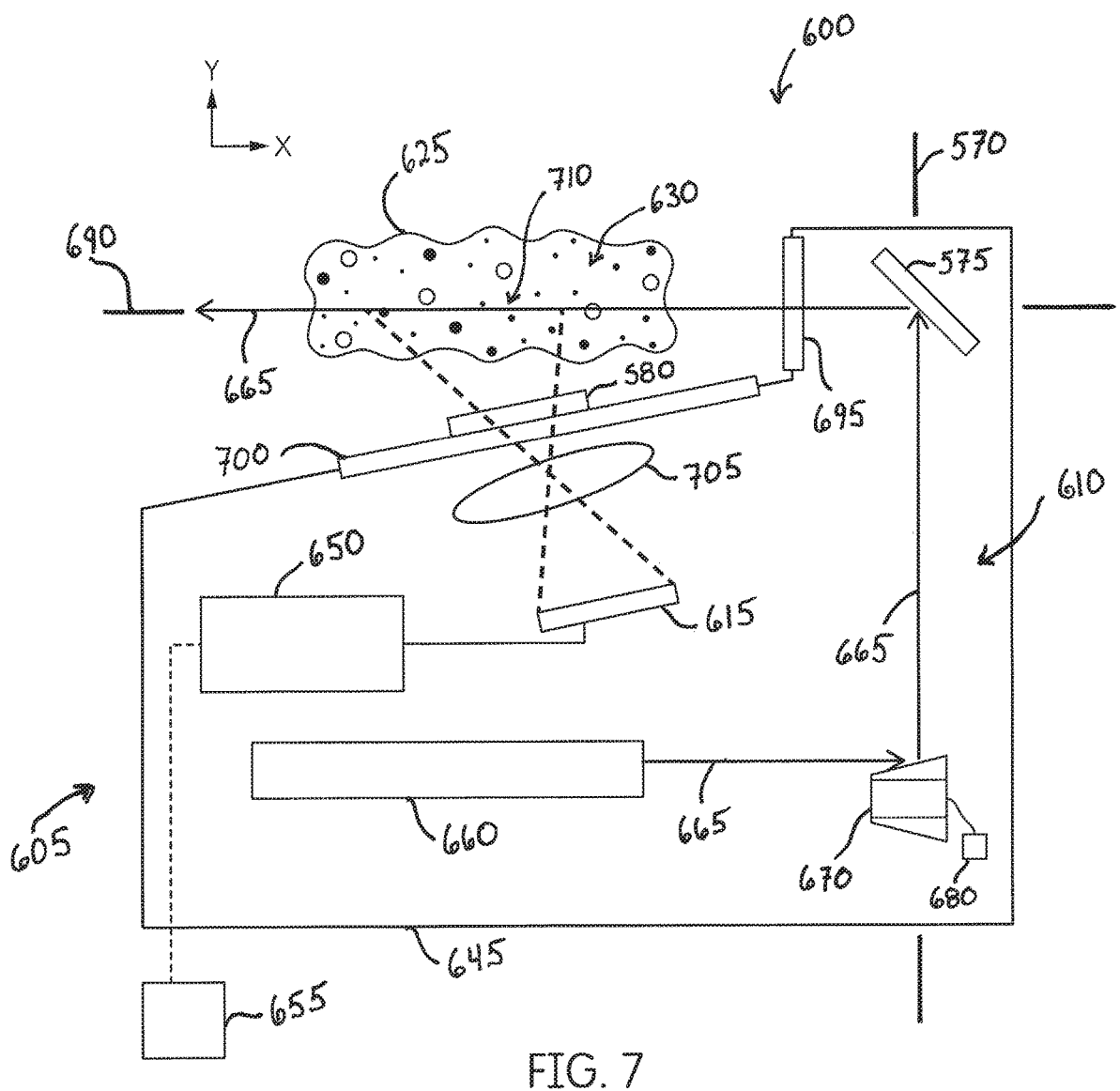
FIG. 7 illustrates an optical sensing and control device according to another embodiment of the invention.

FIG. 7 illustrates an optical device 600 according to another embodiment of the invention. The optical device 600 is similar to the optical device 400; therefore, like components have been given like reference numbers plus 200 and the description focuses on differences between the optical devices 400 and 600. In addition, components or features described with respect to only one or some of the embodiments of the optical device 600 are similarly applicable to other embodiments of the optical devices described herein, and vice versa.

The optical device 600 includes a housing 645 supporting a light plane generator 610 having a light source 660 and an optical component 670 driven by a motor 680, a photodetector 615, a first optical lens 705, and a control assembly 605 having an electronic processor 650 and a controller 655. The light source 660 emits a light beam 665 toward the optical component 670 to direct and move the light beam 665 in an intermediate plane 570 extending between the optical component 670 and a reflector 575. Once the light beam 665 contacts the reflector 575, the reflector 575 directs the light beam 665 into an optical plane 690, which extends into a control volume 625 containing a compound 630, through a first window 695. As the light beam 665 moves within the optical plane 690, the light beam 665 interacts with the compound 630 resulting in scatter of the light beam 665 that is detected by the photodetector 615 within a target area 710 through a second window 700. In other embodiments, the first window 695 and the second window 700 may form a single window. The illustrated second window 700 is obliquely oriented relative to the first window 695 with a second optical lens 580 coupled to the second window 700. The second optical lens 580 increases an intensity of the scattered light within the target area 710 to the photodetector 615. In the illustrated embodiment, the photodetector 615 is obliquely oriented relative to the optical plane 690 so that the photodetector 615 detects obliquely scattered light. Accordingly, the photodetector 615 generates image data that is received by the electronic processor 650, and the electronic processor 650 generates an image that is received by the controller 655 for analysis and control based thereon.

Figure 8:
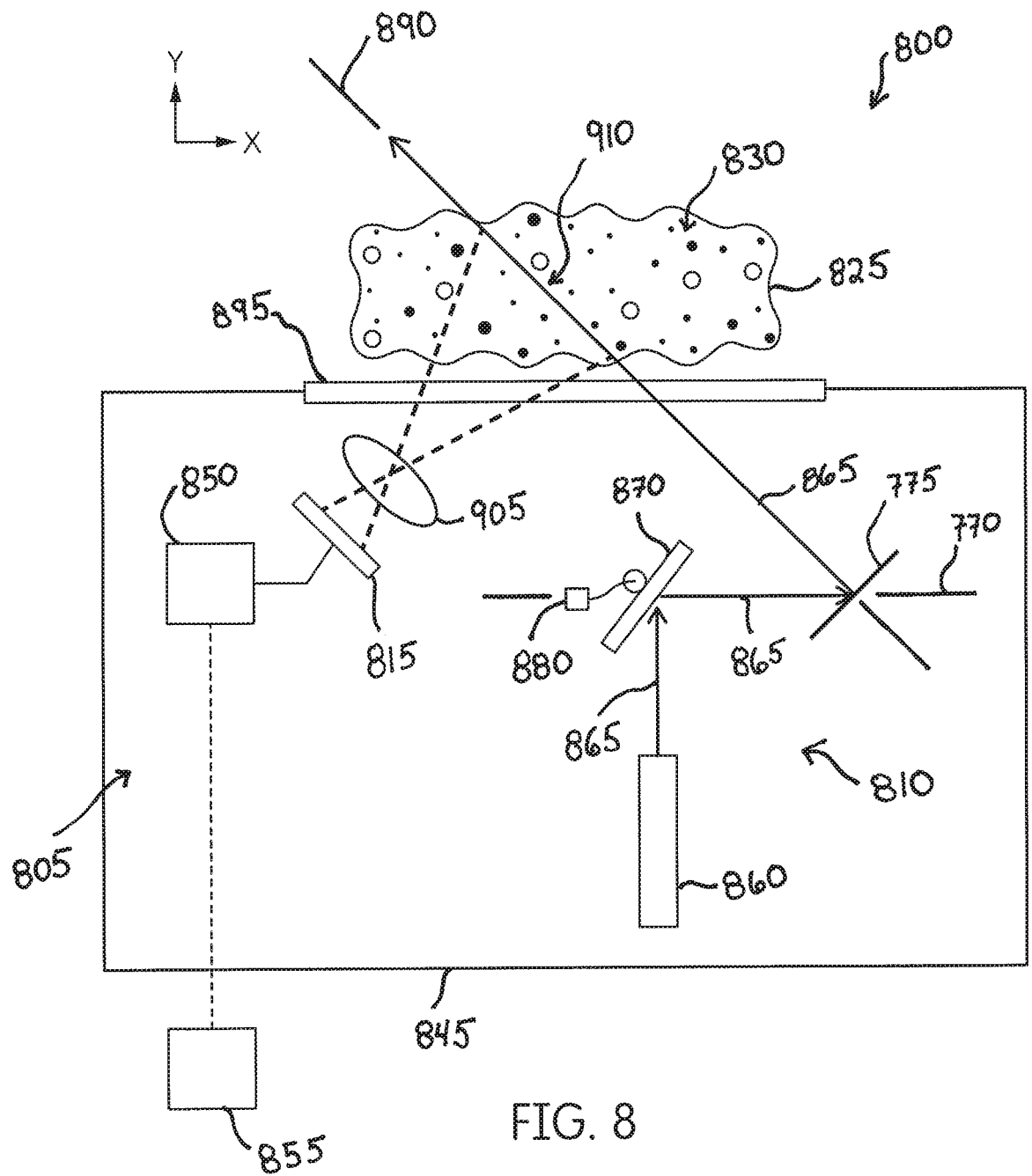
FIG. 8 illustrates an optical sensing and control device according to another embodiment of the invention.

FIG. 8 illustrates an optical device 800 according to another embodiment of the invention. The optical device 800 is similar to the optical device 600; therefore, like components have been given like reference numbers plus 200 and the description focuses on differences between the optical devices 600 and 800. In addition, components or features described with respect to only one or some of the embodiments of the optical device 800 are similarly applicable to other embodiments of the optical devices described herein, and vice versa.

The optical device 800 includes a housing 845 supporting a light plane generator 810 having a light source 860 and an optical component 870 driven by a motor 880. In the illustrated embodiment, the optical component 870 is a pivoting mirror that pivots about an axis extending along a line in the XY plane. In other embodiments, the pivoting mirror 870 may pivot about another axis. The optical device 800 also includes a photodetector 815, an optical lens 905, and a control assembly 805 having an electronic processor 850 and a controller 855. The light source 860 emits a light beam 865 toward the optical component 870 to direct and move the light beam 865 in an intermediate plane 770 extending between the optical component 870 and a reflector 775. Once the light beam 865 contacts the reflector 775, the reflector 775 directs the light beam 865 into an optical plane 890, which extends into a control volume 825 containing a compound 830, through a window 895. The light beam 865 exits the window 895 at approximately a 45 degree angle. As the light beam 865 moves within the optical plane 890, the light beam 865 interacts with the compound 830 resulting in scatter of the light beam 865 that is detected by the photodetector 815 within a target area 910 through the window 895 (the same window that the optical plane 890 extends through). In the illustrated embodiment, the photodetector 815 is oriented perpendicular to the optical plane 890. Accordingly, the photodetector 815 generates image data that is received by the electronic processor 850, and the electronic processor 850 generates an image that is received by the controller 855 for analysis and control based thereon.

Figure 9:
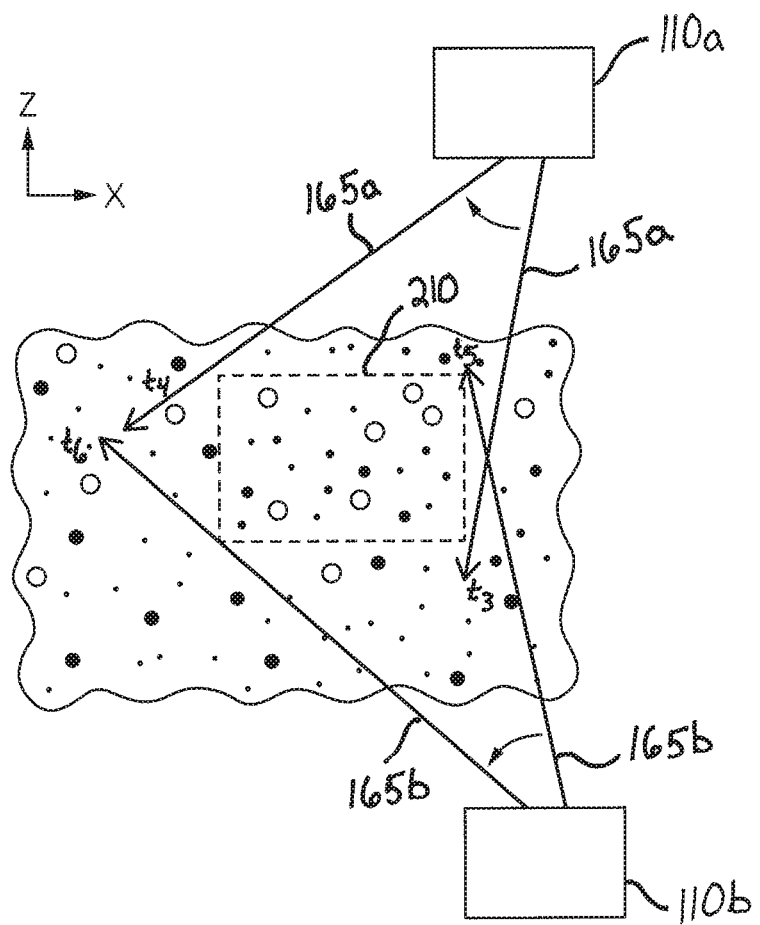
FIG. 9 illustrates a plurality of light plane generators in communication with a control volume according to another embodiment of the invention.

FIG. 9 illustrates a first light generator 110a emitting a first light beam 165a within the optical plane 190 (e.g., the XZ plane) between a first position $t_3$ and a second position $t_4$, and a second light generator 110b emitting a second light beam 165b within the optical plane 190 between a first position $t_5$ and a second position $t_6$. The first and second light generators 110a, 110b are operable to increase the light emitted within the target area 210, and are operable to enable greater consistency of the light within the target area 210 (e.g., the light is distributed more evenly over the target area 210). As such, the image data generated by the photodetector 115 may be improved, and in turn, the effectiveness of the image processing of the controller 155 may be improved. In other embodiments, more than two light beams (e.g., more than two optical devices) may be emitting within the target area 210. In the illustrated embodiment, the first light beam 165a moves in a clockwise direction, and the second light beam 165b moves in the counterclockwise direction. In other embodiments, the first and second light beams 165a, 165b may rotate in the same direction. In further embodiments, the first light generator 110a may focus on a target area that is different (e.g., different area of the compound 130 and/or within different optical planes) than a target area that the second light generator 110b is focusing on. In addition, the optical devices 100, 400, 600, 800 may be modified to include the first and second light generators 110a and 110b as illustrated in FIG. 9.

Figure 10A:
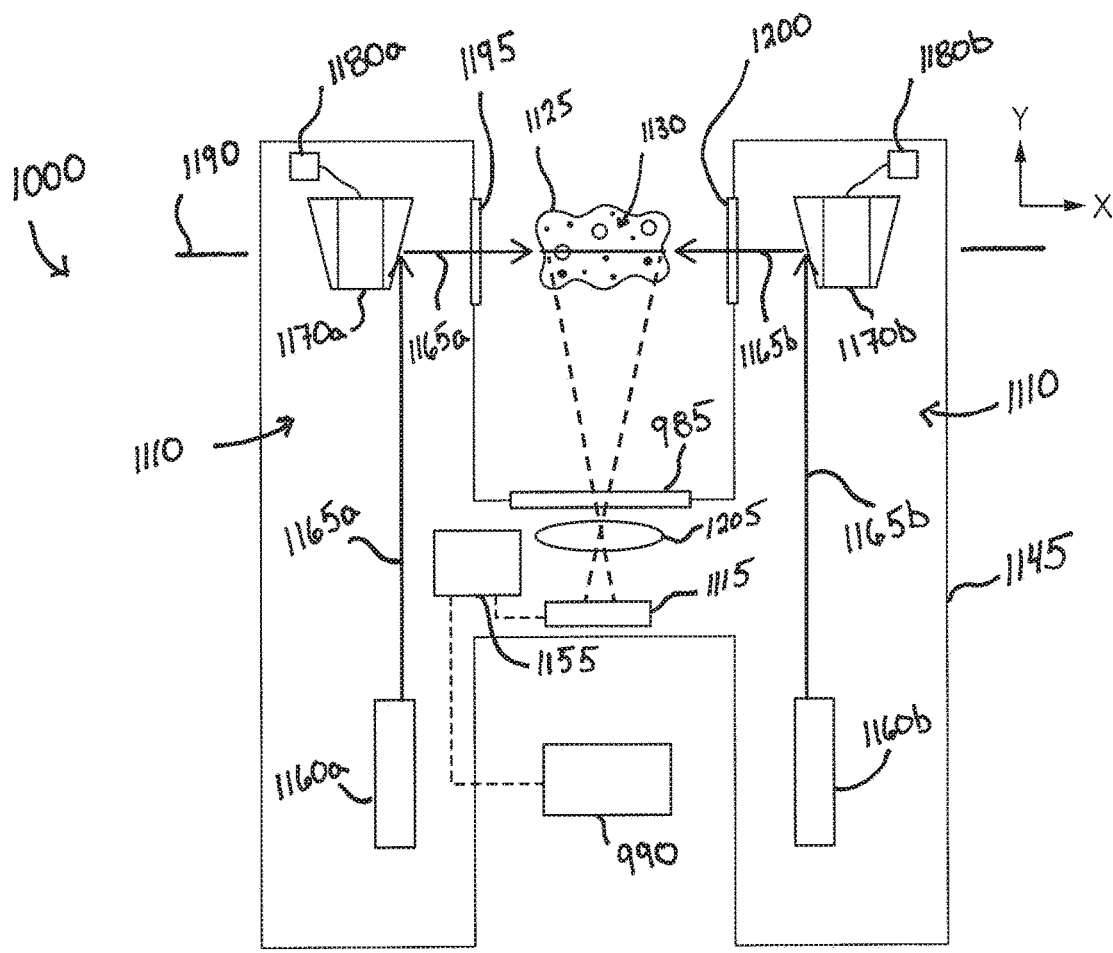
FIG. 10A illustrates a top view of an optical sensing and control device according to another embodiment of the invention.
Figure 10B:
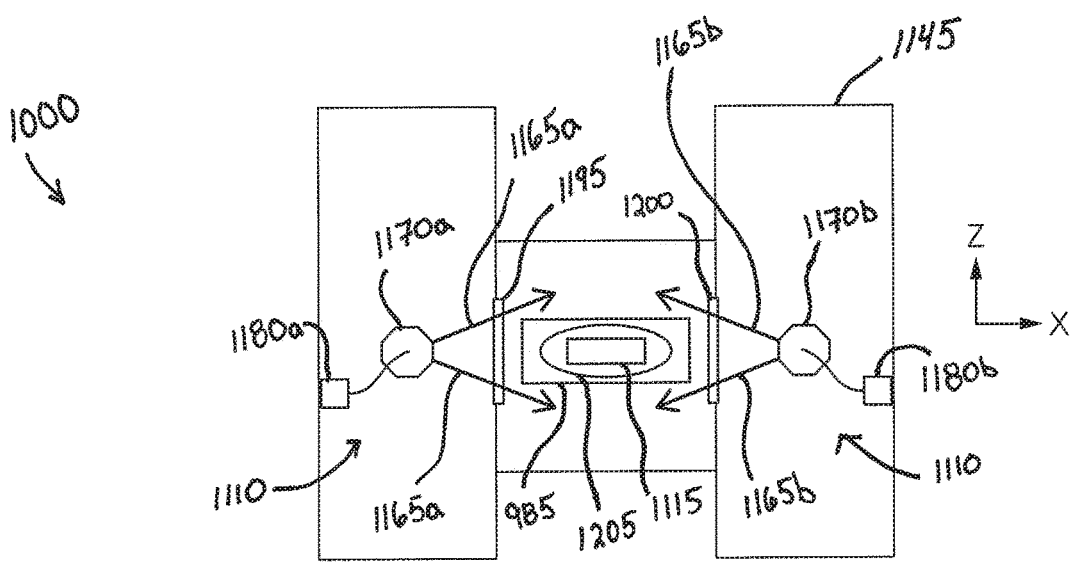
FIG. 10B illustrates a front view of the optical sensing and control device of FIG. 10A.

FIGS. 10A and 10B illustrate an optical device 1000 according to another embodiment of the invention. The optical device 1000 is similar to the optical device 100; therefore, like components have been given like reference numbers plus 900 and the description focuses on differences between the optical devices 100 and 1000. In addition, components or features described with respect to only one or some of the embodiments of the optical device 1000 are similarly applicable to other embodiments of the optical devices described herein, and vice versa.

The optical device 1000 includes a housing 1145 (e.g., an H-shaped housing) supporting a light plane generator 1110 having a first light source 1160a, a second light source 1160b, a first optical component 1170a driven by a first motor 1180a, and a second optical component 1170b driven by a second motor 1180b. The first light source 1160a emits a first light beam 1165a toward the first optical component 1170a to direct and move the first light beam 1165a in an optical plane 1190 through a first window 1195. Simultaneously or in phase with the first light source 1160a, the second light source 1160b emits a second light beam 1165b toward the second optical component 1170b to direct and move the second light beam 1165b in the optical plane 1190 through a second window 1200. As such, both the first and second light beams 1165a, 1165b interact with a compound 1130 contained within a control volume 1125 resulting in first and second scatters of the first and second light beams 1165a, 1165b, respectively. The first and second scatters are then detected by a photodetector 1115 through a third window 985 and an optical lens 1205. Accordingly, the photodetector 1115 generates image data that is received by a controller 1155, and the controller 1155 generates an image of the compound 1130 based on the image data. The illustrated controller 1155 may also control activation of the first and second light sources 1160a, 1160b and angular velocity of the first and second optical components 1170a, 1170b. Furthermore, the control assembly 1105 includes a display 990 in communication with the controller 1155 configured to display real-time (e.g., instantaneous) analysis of the compound 1130 to an operator. For example, the controller 1155 may analyze and show on the display 990 an indication representative of the number of particles in the compound 1130 (e.g., size/frequency distribution), the specific density of the compound 1130 (based on a ratio of the standard deviation of particle size to average particle size), the size distribution (e.g., n larger particles in a first area of the sample, m smaller particles in the first area, p larger particles in a second area, q smaller particles in the smaller area), or a nearest neighbor distance analysis. The display 1130 may be integrated into the housing 1145 or separate from the housing 1145, and the display 1130 may be in communication with the controller 1155 by a wired connection or a wireless connection. Furthermore, a power source may be coupled to the housing 1145 to provide power to at least one of the controller 1155, the first and second light sources 1160a, 1160b, the display 990, and the first and second motors 1180a, 1180b.

Figure 11:
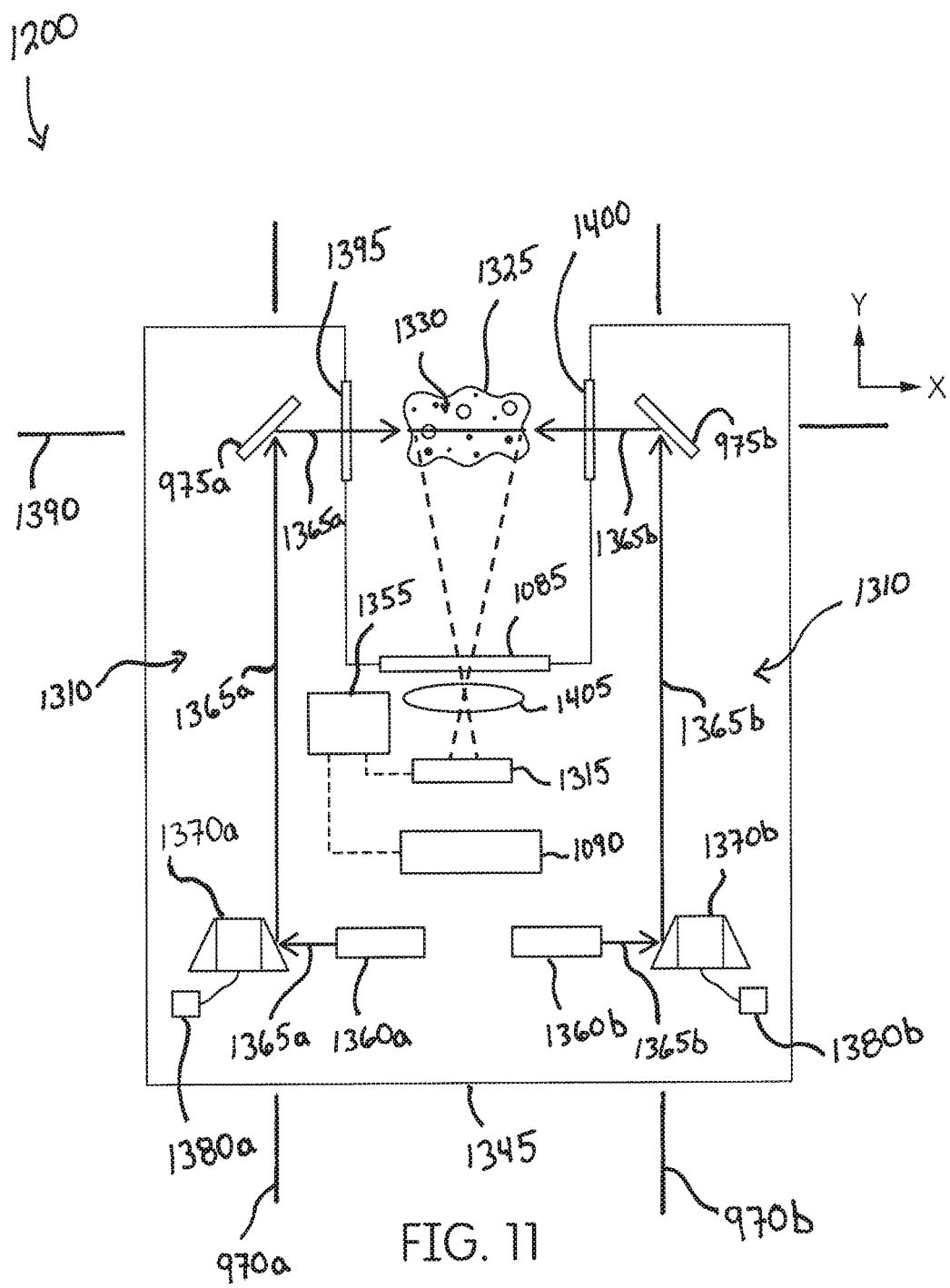
FIG. 11 illustrates an optical sensing and control device according to another embodiment of the invention.

FIG. 11 illustrates an optical device 1200 according to another embodiment of the invention. The optical device 1200 is similar to the optical device 1000; therefore, like components have been given like reference numbers plus 200 and the description focuses on differences between the optical devices 1000 and 1200. In addition, components or features described with respect to only one or some of the embodiments of the optical device 1200 are similarly applicable to other embodiments of the optical devices described herein, and vice versa.

The optical device 1200 includes a housing 1345 supporting a light plane generator 1310 having a first light source 1360a, a second light source 1360b, a first optical component 1370a driven by a first motor 1380a, and a second optical component 1370b driven by a second motor 1380b. The first light source 1360a emits a first light beam 1365a toward the first optical component 1370a to direct and move the first light beam 1365a in a first intermediate plane 970a toward a first reflector 975a. Thereafter, the first light beam 1365a extends into an optical plane 1390 through a first window 1395. Simultaneously or in phase with the first light source 1360a, the second light source 1360b emits a second light beam 1365b toward the second optical component 1370b to direct and move the second light beam 1365b in a second intermediate plane 970b toward a second reflector 975b. Thereafter, the second light beam 1365b extends into the optical plane 1390 through a second window 1400. As such, both the first and second light beams 1365a, 1365b interact with a compound 1330 contained within a control volume 1325 resulting in first and second scatters of the first and second light beams 1365a, 1365b, respectively. The first and second scatters are then detected by a photodetector 1315 through a third window 1085 and an optical lens 1405. Accordingly, the photodetector 1315 generates image data that is received by a controller 1355, and the controller 1355 generates an image of the compound 1330 based from the image data. The illustrated controller 1355 may also control activation of the first and second light sources 1360a, 1360b and angular velocity of the first and second optical components 1370a, 1370b. Furthermore, the control assembly 1305 includes a display 1090 in communication with the controller 1355 configured to display real-time (e.g., instantaneous) analysis of the compound 1130 to an operator.

In some embodiments, the first and second light sources 1360a, 1360b may emit a red or blue laser. Generally, blue lasers can result in increased scattering of light from the compound 1330, which can then be more easily captured by the photodetector 1315. In some instances, blue lasers may also cause the compound 1330 to fluoresce, which can then be captured by the photodetector 1315. The fluorescence properties of different types of particles vary. Accordingly, image analysis software can be used to identify a type of particle based the different wavelengths of the fluorescence captured in the image. Similarly, the light sources of other light generators described herein (e.g., light source 160, 660, etc.) may be red or blue lasers and can be used to cause compounds being scanned to fluoresce, which can similarly be detected by the photodetector associated with these light sources.

Figure 12:
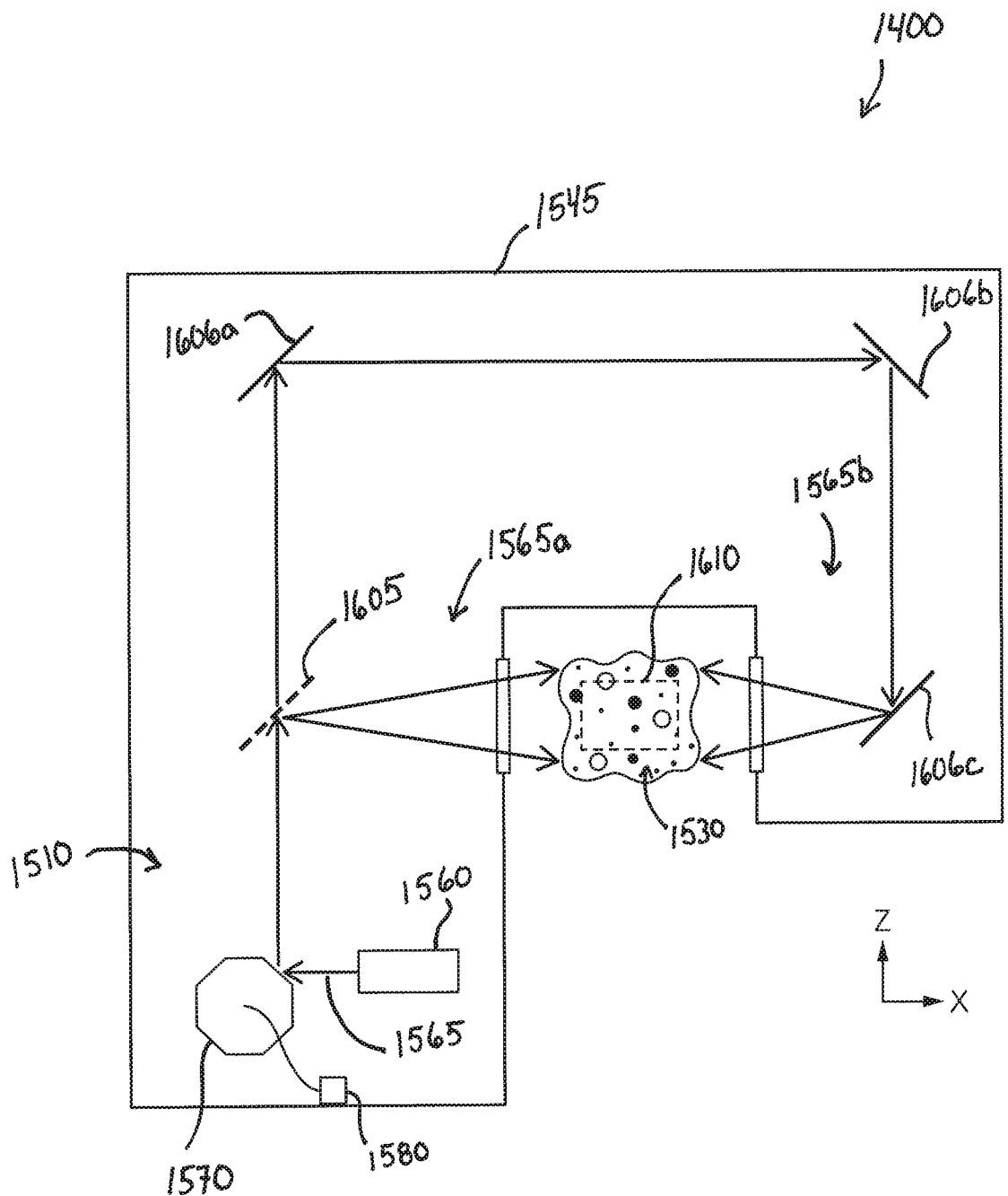
FIG. 12 illustrates an optical sensing and control device according to another embodiment of the invention.

FIG. 12 illustrates an optical device 1400 according to another embodiment of the invention. The optical device 1400 is similar to the optical device 400; therefore, like components have been given like reference numbers plus 1100 and the description focuses on differences between the optical devices 400 and 1400. In addition, components or features described with respect to only one or some of the embodiments of the optical device 1400 are similarly applicable to other embodiments of the optical devices described herein, and vice versa.

The optical device 1400 includes a housing 1545 supporting a light plane generator 1510 having a light source 1560 and an optical component 1570 driven by a motor 1580. The light source 1560 emits a light beam 1565 toward the optical component 1570 to direct and move the light beam 1565 toward an optical splitter 1605. The optical splitter 1605 is configured to separate the light beam 1565 into at least a first portion 1565a and a second portion 1565b. The optical splitter 1605 also directs the first portion 1565a toward a compound 1530 to move across a target area 1610. The optical splitter 1605 further directs the second portion 1565b toward a first reflector 1606a so that the second portion 1565b reflects off of the first reflector 1606a and is directed toward a second reflector 1606b, reflects off of the second reflector 1606b and is directed toward a third reflector 1606c, and is reflected off of the third reflector 1606c to be directed toward the compound 1530 to move across the target area 1610.

Figure 13:
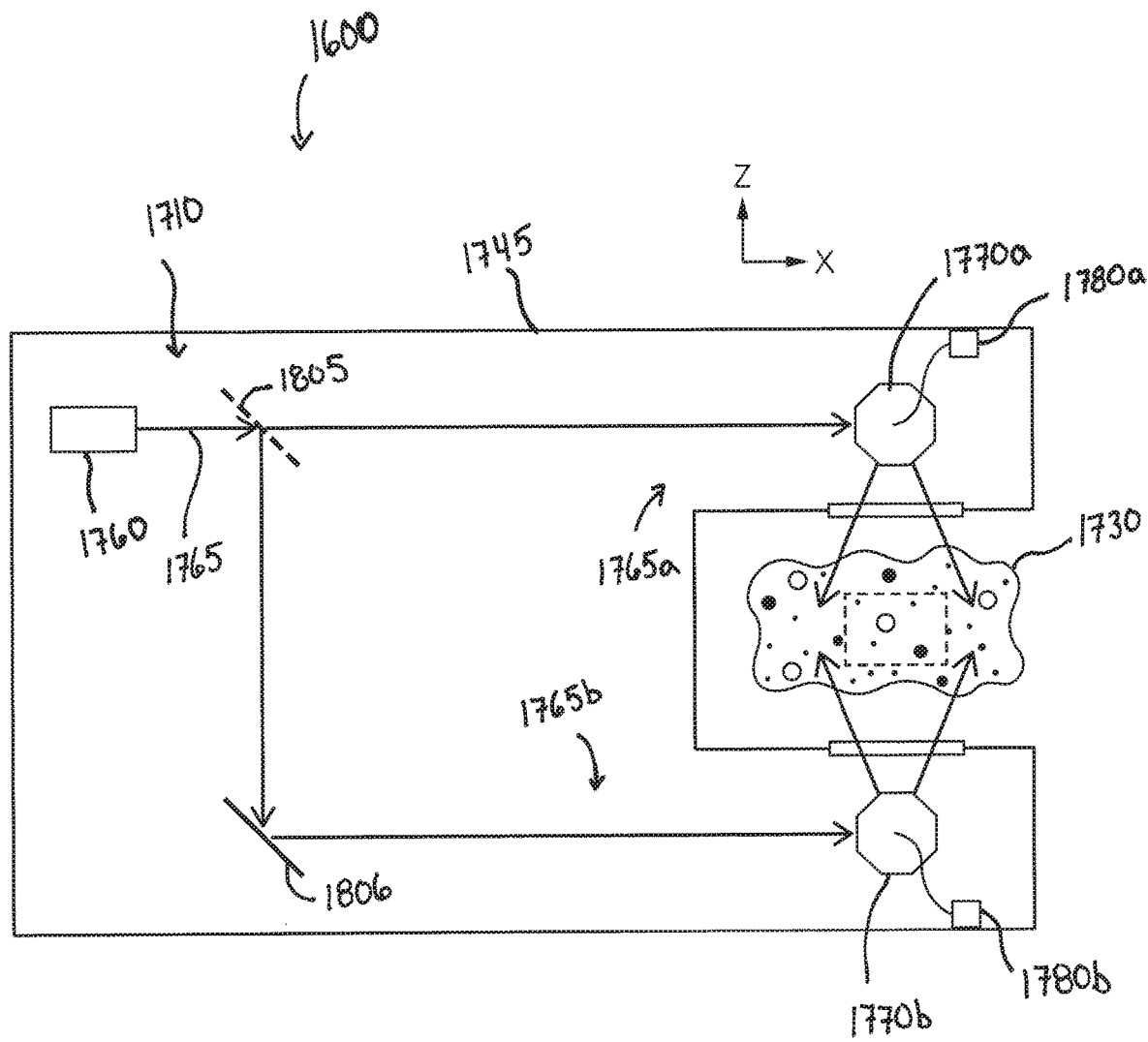
FIG. 13 illustrates an optical sensing and control device according to another embodiment of the invention.

FIG. 13 illustrates an optical device 1600 according to another embodiment of the invention. The optical device 1600 is similar to the optical device 1400; therefore, like components have been given like reference numbers plus 300 and the description focuses on differences between the optical devices 1400 and 1600. In addition, components or features described with respect to only one or some of the embodiments of the optical device 1600 are similarly applicable to other embodiments of the optical devices described herein, and vice versa.

The optical device 1600 includes a housing 1745 supporting a light plane generator 1710 having a light source 1760, a splitter 1805, a first optical component 1770a driven by a first motor 1780a, and a second optical component 1770b driven by a second motor 1780b. The light source 1760 emits a light beam 1765 toward the optical splitter 1805, and the optical splitter 1805 separates the light beam 1765 into a first portion 1765a and a second portion 1765b. The first portion 1765a is directed to the first optical component 1770a to be directed towards a compound 1730. The second portion 1765b is directed toward a reflector 1806 to be directed toward the second optical component 1770b and to be directed toward the compound 1730.

Figure 14:
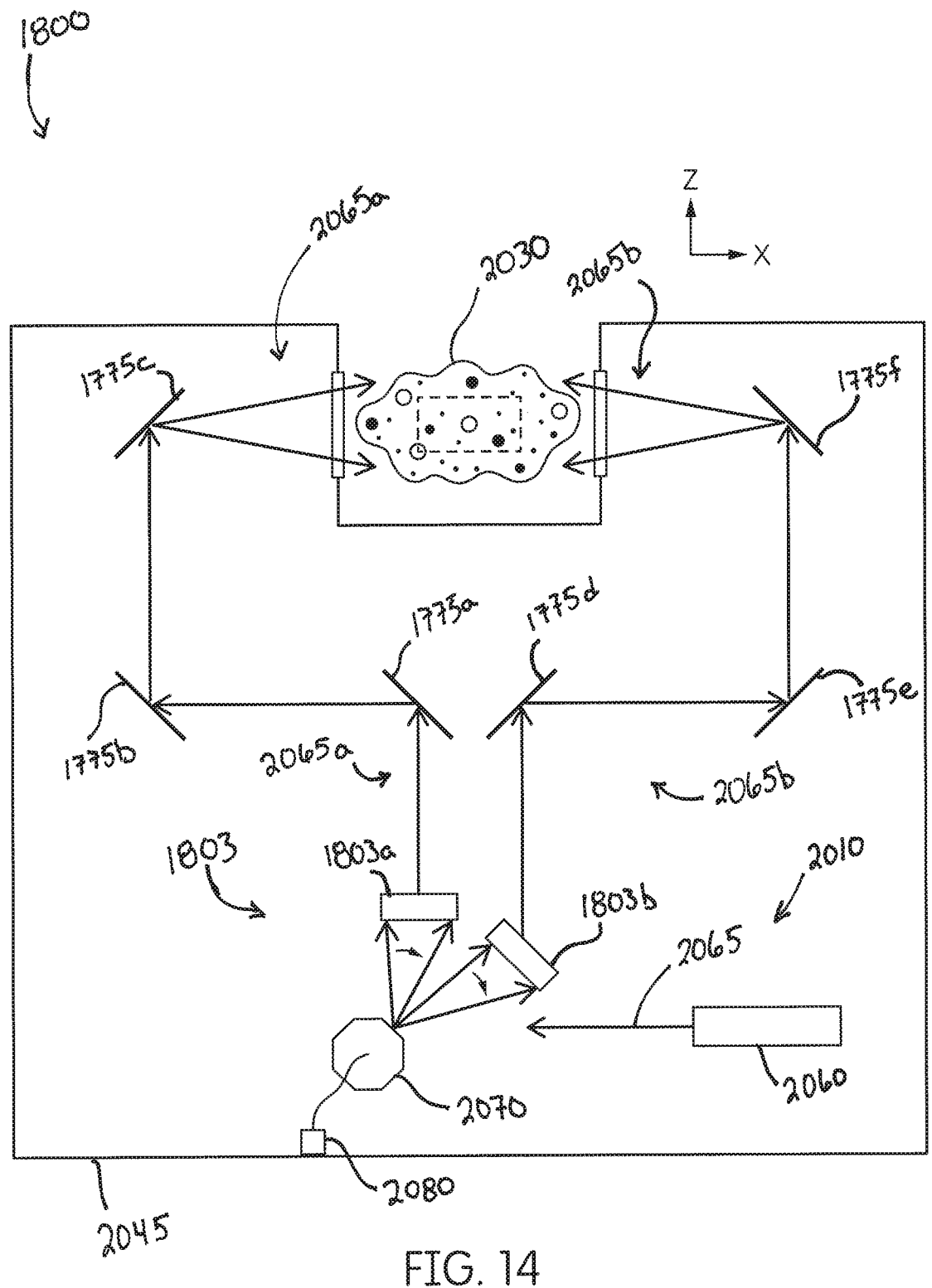
FIG. 14 illustrates an optical sensing and control device according to another embodiment of the invention.

FIG. 14 illustrates an optical device 1800 according to another embodiment of the invention. The optical device 1800 is similar to the optical device 1600; therefore, like components have been given like reference numbers plus 300 and the description focuses on differences between the optical devices 1600 and 1800. In addition, components or features described with respect to only one or some of the embodiments of the optical device 1800 are similarly applicable to other embodiments of the optical devices described herein, and vice versa.

The optical device 1800 includes a housing 2045 supporting a light plane generator 2010 having a light source 2060 and an optical component 2070 driven by a motor 2080. The light source 2060 emits a light beam 2065 toward the optical component 2070, and the optical component 2070 directs the light beam 2065 toward a refracting assembly 1803 including a first refracting member 1803a and a second refracting member 1803b. As the optical component 2070 rotates, the light beam 2065 passes through the first refracting member 1803a to produce a first light beam portion 2065a and then passes through the second refracting member 1803b to produce a second light beam portion 2065b. The first light beam portion 2065a is then directed to a first reflector 1775a, which is directed to a second reflector 1775b, which is directed to a third reflector 1775c, to be directed toward a compound 2030. Thereafter, the second light beam portion 2065b is then directed to a fourth reflector 1775d, which is directed to a fifth reflector 1775e, which is directed to a sixth reflector 1775f, to be directed toward the compound 2030. In another embodiment, the first and/or second light beam portions 2065a, 2065b may be reflected by more or less than three reflectors before extending into the compound 2030.

A photodetector (not shown) is included for each of the optical devices 1400, 1600, and 1800, but, like the photodetectors described above (e.g., photodetector 115), it is spaced from the compound 1530 along the Y-axis to capture image data for the target area 1610. Accordingly, these photodetectors are not illustrated in the views of the optical devices provided in FIGS. 12, 13, and 14.

As noted above, components or features described with respect to only one or some of the embodiments of the optical devices are similarly applicable to other embodiments of the optical devices described herein. For example, the various optical devices (e.g., 400, 600, 800, and 1200) may be modified to remove a reflector (e.g., the reflector 375 in the case of the optical device 400) and the associated light generators and optical components re-positioned to direct light out of a window of the optical device without the reflector as illustrated in the optical device 100 of FIG. 2. Additionally, the various optical devices (for example, the optical devices 100, 400, 600, 800, 1000, 1200, 1400, and 1600, 1800), may have: one or more windows and or photodetectors positioned at oblique angles as shown in the optical device 600 of FIG. 7; a single window as shown in the optical device 800 of FIG. 8; a pivoting mirror or prism as an optical component, in place of a rotating mirror or prism, as shown in the optical device 800 of FIG. 8; multiple light generators and optical components as shown in FIGS. 10A-B; a beam splitter and reflectors positioned to generate multiple optical planes as shown in the optical device 1400 or 1600 of FIGS. 12 and 13; and multiple optical planes using the arrangement illustrated in the optical device 1800 of FIG. 14. Some embodiments include further combinations of components of the various optical devices as well.

Referring back to FIG. 5, while the method 245 of FIG. 5 is described with respect to the optical device 100 (within the liquid treatment system 215 of FIG. 4), the method 245 is similarly applicable to the other optical devices described herein, including the optical devices 400, 600, 800, 1000, 1200, 1400, and 1600, 1800, and the various embodiments thereof, and to any of these optical devices employed in other systems including microflotation system monitoring, drinking water quality monitoring, ballast monitoring, emissions monitoring, ice concentration monitoring, body of water pollution monitoring, crystallization monitoring, paper fiber flocculation monitoring, emulsification monitoring, and dissolution monitoring, and the like. For these alternative system, control of the output device 120 in step 265 of the method 245 may be modified for the particular process variables applicable to the system being monitored. Further, in some embodiments, the output device 120 is controlled in step 265 to provide an alert (e.g., one or more of an audible, tactile, and visual alert) when a particular monitored variable exceeds some threshold.

Figure 15:
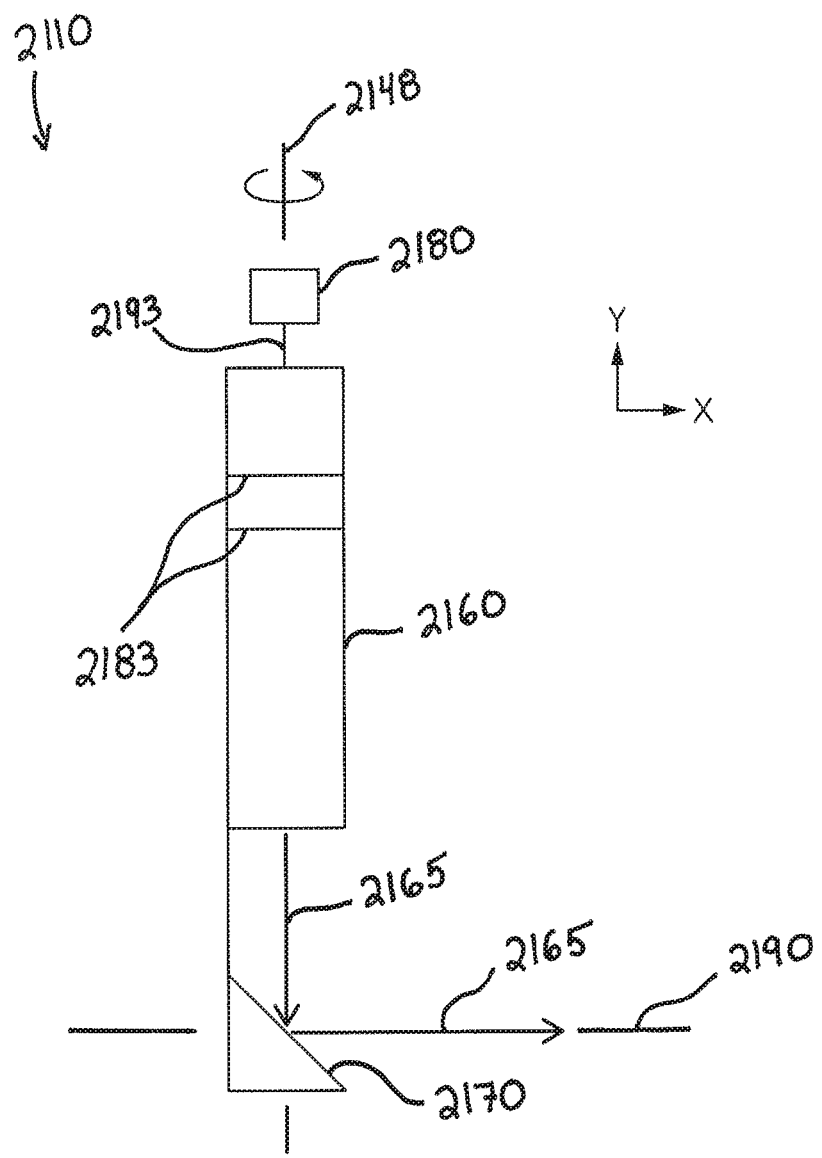
FIG. 15 illustrates a light plane generator of an optical sensing and control device according to another embodiment of the invention.

FIG. 15 illustrates a light plane generator 2110 according to another embodiment of the invention. The light plane generator 2110 is similar to the light plane generator 110 and may be used in any of the optical devices described herein (e.g., the optical device 100, 400, etc.); therefore, like components have been given like reference numbers plus 2000 and the description focuses on differences between the light plane generators 110, 2110. In addition, components or features described with respect to only one or some of the embodiments of the light plane generator 2110 are similarly applicable to other embodiments of the light plane generator described herein, and vice versa.

The light plane generator 2110 includes a light source 2160 driven by a motor 2180 about a rotational axis 2148. In particular, the light source 2160 is coupled to a rotational shaft 2193 of the motor 2180 such that driving the rotational shaft 2193 by the motor 2180 rotationally drives the light source 2160. The light source 2160 further includes conductive rings 2183 electrically coupled to a power source (e.g., via brushes) to power the light source 2160. An optical component 2170 (e.g., a mirror or prism) is coupled to the light source 2160 for rotation therewith about the rotational axis 2148. The light source 2160 is operable to emit a light beam 2165 toward the optical component 2170 so that the optical component 2170 moves the light beam 2165 in an optical plane 2190. In the illustrated embodiment, the optical plane 2190 is perpendicular to the rotational axis 2148; however, in other embodiments, the optical plane 2190 may be obliquely oriented relative to the rotational axis 2148. The optical plane 2190, like the optical plane 190, extends into a control volume (not shown), the scattering of which may be detected using a photodetector as previous described. In other words, the light plane generator 2110 may be substituted into and replace the light generator(s) of any of the previous optical devices described herein.

Figure 16:
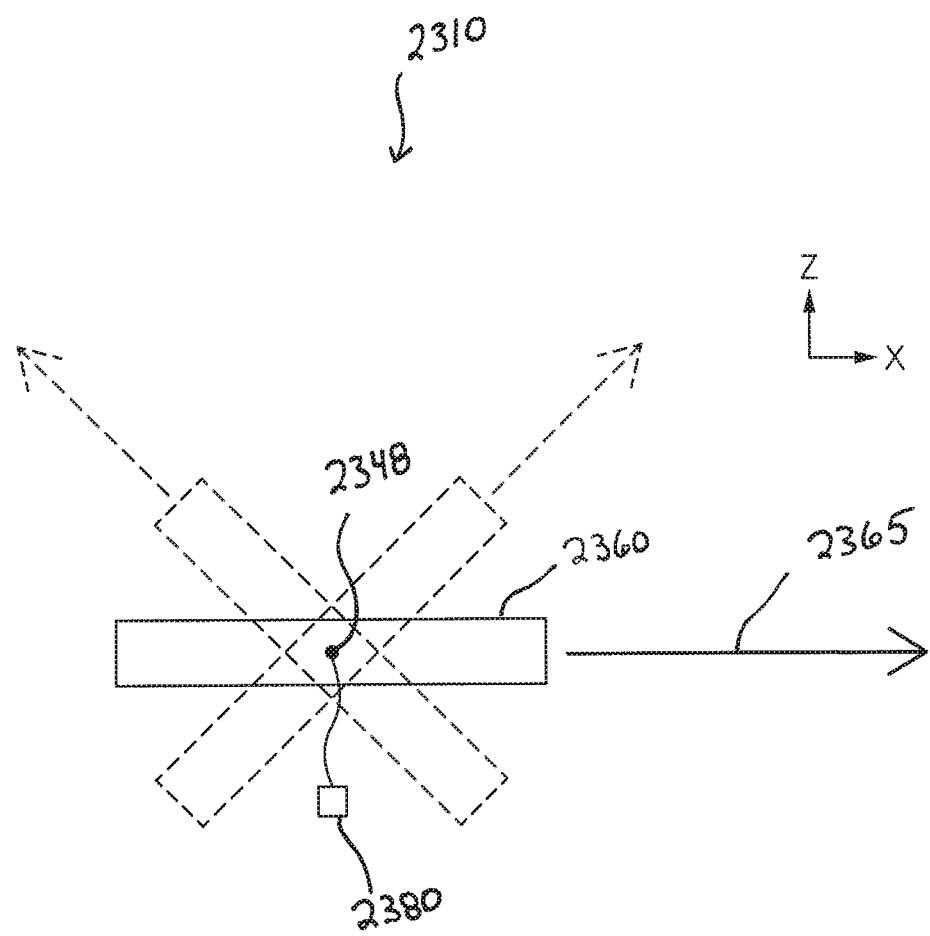
FIG. 16 illustrates a light plane generator of an optical sensing and control device according to another embodiment of the invention.

FIG. 16 illustrates a light plane generator 2310 according to another embodiment of the invention. The light plane generator 2310 is similar to the light plane generator 2110 and may be used in any of the optical devices described herein (e.g., the optical device 100, 400, etc.); therefore, like components have been given like reference numbers plus 200 and the description focuses on differences between the light plane generators 2110, 2310. In addition, components or features described with respect to only one or some of the embodiments of the light plane generator 2310 are similarly applicable to other embodiments of the light plane generator described herein, and vice versa.

The light plane generator 2310 includes a light source 2360 driven by a motor 2380 about a rotational axis 2348. The light source 2360 is operable to emit a light beam 2365, and as the light source 2360 rotates about the rotational axis 2348, the light beam 2365 moves within an optical plane (i.e., the XZ plane). This optical plane, like the optical plane 190, extends into a control volume (not shown), the scattering of which may be detected using a photodetector as previous described. In other words, the light plane generator 2310 may be substituted into and replace the light generator(s) of any of the previous optical devices described herein.

Although the invention has been described in detail with reference to certain preferred embodiments, variations and modifications exist within the scope and spirit of one or more independent aspects of the invention as described.

The invention claimed is:

1. An optical sensing and control device comprising:
   a light source emitting a light beam;
   an optical component in communication with the light beam to receive the light beam from the light source, the optical component driven by a motor for the optical component to rotate about an axis relative to the light beam;
   a control assembly in communication with the motor to rotate the optical component at a selected plurality of revolutions per minute about the axis such that the optical component is configured to move the light beam in a plane, the plane extending into an area such that the light beam interacts with particles in the area producing a scattering of the light beam; and
   a photodetector in communication with the particles within the plane, the photodetector configured to generate image data in response to the scattering of the light beam while the optical component is driven about the axis.

2. The optical sensing and control device of claim 1, further comprising a housing that supports the light source, the optical component, and the photodetector, wherein the optical component is rotatable or pivotable relative to the housing.

3. The optical sensing and control device of claim 2, wherein the optical component includes a first planar surface and a second planar surface, wherein the first planar surface is obliquely oriented relative to the second planar surface, and wherein the optical component is driven by the motor between about 1 revolution per minute and about 60,000 revolutions per minute for the first planar surface to interact with the light beam to move the light beam in the plane and for the second planar surface to interact with the light beam to move the light beam in the plane.

4. The optical sensing and control device of claim 2, further comprising a reflector that receives the light beam, wherein the reflector is positioned between the light source and the optical component or the reflector is positioned between the optical component and the area.

5. The optical sensing and control device of claim 2, wherein the housing includes at least one window, and wherein the light beam is configured to pass through the at least one window to interact with the particles, and wherein the photodetector is in visual communication with the particles within the plane through the at least one window.

6. The optical sensing and control device of claim 1, further comprising an electronic processor, wherein the image data generated by the photodetector is received by the electronic processor, and wherein the electronic processor is configured to generate an image based on the image data.

7. The optical sensing and control device of claim 1, further comprising a lens positioned between the photodetector and the plane, wherein the lens is configured to focus the photodetector on the plane.

8. The optical sensing and control device of claim 1, wherein the photodetector is focused on a target area oriented within the plane.

9. The optical sensing and control device of claim 1, wherein the light source is a first light source, the light beam is a first light beam, the optical component is a first optical component, the plane is a first plane, and the scattering of the first light beam is a first scattering, wherein the optical sensing and control device further comprising
a second light source emitting a second light beam; and
a second optical component in communication with the second light beam, the second optical component configured to move the second light beam in a second plane, the second plane extending into the area such that the second light beam interacts with the particles producing a second scattering of the second light beam.

10. The optical sensing and control device of claim 9, wherein the photodetector is configured to detect the first and second scatterings of the first and second light beams.

11. The optical sensing and control device of claim 1, wherein the plane is a first plane, and wherein the optical sensing and control device further comprising
an optical splitter configured to separate the light beam into a first portion and a second portion, wherein the first portion is configured to form the first plane, and the second portion is configured to form a second plane.

12. The optical sensing and control device of claim 1, wherein the plane is a first plane, and wherein the optical sensing and control device further comprising
a first refracting member configured to separate the light beam into a first portion, wherein the first portion is configured to form the first plane; and
a second refracting member configured to separate the light beam into a second portion, wherein the second portion is configured to form a second plane.

13. A method of determining a process variable of a compound contained within a control volume, the method comprising:
emitting a light beam from a light source toward an optical component such that the optical component receives the light beam;
rotating the optical component one revolution relative to the light beam such that a first surface of the optical component moves the light beam from a first position to a second position in a plane during the one revolution of the optical component and a second surface of the optical component moves the light beam from the first position to the second position in the plane during the one revolution of the optical component, the plane extending into the compound for the light beam to interact with the compound producing a scattering of the light beam;
generating image data from the scattering of the light beam with a photodetector; and
analyzing the image data to determine the process variable.

14. The method of claim 13, wherein analyzing the image data to determine the process variable includes generating an image from the image data with an electronic processor and analyzing the image.

15. The method of claim 14, further comprising analyzing the image to control an output device that is configured to control the process variable.

16. The method of claim 15, further comprising controlling the process variable by a controlling step selected from the group consisting of changing a temperature of the compound, introducing a chemical into the control volume, changing a mixing rate of at least two portions of the compound, controlling an inlet valve of the control volume, and controlling an outlet valve of the control volume.

17. A liquid treatment system comprising:
a control volume containing a compound;
an output device in communication with the control volume, the output device configured to control a process variable of the compound; and
an optical sensing and control device in communication with the compound, the optical sensing and control device including
a light source emitting a light beam,
an optical component including a first surface and a second surface in communication with the light beam to receive the light beam from the light source, the optical component rotatable one revolution relative to the light beam such that the first surface of the optical component is configured to move the light beam in a plane from a first position to a second position during the one revolution of the optical component and the second surface of the optical component is configured to move the light beam in the plane from the first position to the second position during the one revolution of the optical component, the plane extending into the compound such that the light beam interacts with the compound producing a scattering of the light beam, and
a photodetector in communication with the compound within the plane, the photodetector configured to detect the scattering of the light beam;
wherein the output device is configured to control the process variable based on the scattering of the light by a control function selected from the group consisting of changing a temperature of the compound, introducing a chemical into the control volume, changing a mixing rate of at least two portions of the compound, controlling an inlet valve of the control volume, and controlling an outlet valve of the control volume.

18. The liquid treatment system of claim 17, wherein the optical sensing and control device includes a control assembly that receives image data from the photodetector based on the scattering of the light beam.

19. The liquid treatment system of claim 18, wherein the control assembly generates an image based on the image data, and wherein the control assembly controls the output device based on the image.

20. The liquid treatment system of claim 19, wherein the optical sensing and control device further includes a housing that supports the light source, the optical component, and the photodetector.

\* \* \* \* \*